(12) United States Patent
Murphy et al.

(10) Patent No.: US 11,781,972 B2
(45) Date of Patent: Oct. 10, 2023

(54) TECHNIQUES FOR SELECTION OF LIGHT SOURCE CONFIGURATIONS FOR MATERIAL CHARACTERIZATION

(71) Applicant: X Development LLC, Mountain View, CA (US)

(72) Inventors: Gearoid Murphy, Mountain View, CA (US); Diosdado Rey Banatao, Los Altos Hills, CA (US); Artem Goncharuk, Mountain View, CA (US); Neil Treat, Los Gatos, CA (US)

(73) Assignee: X Development LLC, Mountain View, CA (US)

( * ) Notice: Subject to any disclaimer, the term of this patent is extended or adjusted under 35 U.S.C. 154(b) by 269 days.

(21) Appl. No.: 16/949,601

(22) Filed: Nov. 5, 2020

(65) Prior Publication Data

US 2022/0136959 A1     May 5, 2022

(51) Int. Cl.
  G01N 21/25 (2006.01)
  G01N 21/3563 (2014.01)
  (Continued)

(52) U.S. Cl.
  CPC ....... G01N 21/255 (2013.01); G01N 21/3563 (2013.01); G01N 33/442 (2013.01); G06N 3/126 (2013.01)

(58) Field of Classification Search
  CPC . G01N 21/255; G01N 21/3563; G01N 33/442
  See application file for complete search history.

(56) References Cited

U.S. PATENT DOCUMENTS

| | | | |
|---|---|---|---|
| 5,435,309 A * | 7/1995 | Thomas | A61B 5/6843 |
| | | | 600/326 |
| 5,857,462 A | 1/1999 | Thomas et al. | |

(Continued)

FOREIGN PATENT DOCUMENTS

| | | |
|---|---|---|
| WO | 0127597 | 4/2001 |
| WO | 2014137322 | 9/2014 |
| WO | 2015195746 | 12/2015 |

OTHER PUBLICATIONS

Galyanin et al., "Selecting optimal wavelength intervals for an optical sensor: A case study of milk fat and total protein analysis in the region 400-1100 nm." Sensors and Actuators B: Chemical 218:97-104 (2015).

(Continued)

Primary Examiner — John E Breene
Assistant Examiner — Dacthang P Ngo
(74) Attorney, Agent, or Firm — Kilpatrick Townsend & Stockton LLP

(57) ABSTRACT

Techniques for selecting a spectroscopic light source include obtaining a light source dataset and a spectroscopic dataset, initializing a genetic algorithm, selecting a first individual solution and a second individual solution from an initial generation of solutions, generating a new individual solution from the first and second individual solutions by combining their respective chromosome encodings, evaluating a specificity of the new individual solution to a target material, adding the new individual solution to a new generation of solutions, populating the new generation of solutions with a plurality of additional individual solutions, generating one or more descendent generations of solutions by iterating the genetic algorithm, selecting one or more implementation individual solutions exhibiting a threshold specificity to the target material, and outputting the one or more implementation individual solutions.

24 Claims, 6 Drawing Sheets

(51) Int. Cl.
 *G01N 33/44* (2006.01)
 *G06N 3/126* (2023.01)

(56) References Cited

U.S. PATENT DOCUMENTS 7,676,442 B2   3/2010   Ben-Hur et al.
10,509,223 B2 * 12/2019  Shen ..................... G06N 3/126

OTHER PUBLICATIONS

Mankar et al., "Selecting optimal features from Fourier transform infrared spectroscopy for discrete-frequency imaging" Analyst, 143(5):1147-1156 (2018).
Kole et al., "Discrete frequency infrared microspectroscopy and imaging with a tunable quantum cascade laser." Anal Chem., 84(23):10366-10372 (2012).
Van Den Broek, et al., "Optimal Wavelength Range Selection by a Genetic Algorithm for Discrimination Purposes in Spectroscopic Infrared Imaging," Appl. Spectrosc. 51, 1210-1217 (1997).
Bogomolov et al., "Development and testing of an LED-based near-infrared sensor for human kidney tumor diagnostics." Sensors, 17, 1914, pp. 1-17 (2017).
Niazi et al., "Genetic algorithms in chemometrics." Journal of Chemometrics 26.6 (2012): 345-351. Journal of Cheminformatics, 26, pp. 345-351 (2012).
International Application No. PCT/US2021/057896, International Search Report and Written Opinion, dated Feb. 23, 2022, 13 pages.

\* cited by examiner

TECHNIQUES FOR SELECTION OF LIGHT SOURCE CONFIGURATIONS FOR MATERIAL CHARACTERIZATION

FIELD

The present disclosure relates to spectroscopy, and in particular to techniques for configuring light sources and arrays of light sources using characteristic spectra of materials.

BACKGROUND

Plastic products are predominantly single-use and frequently not recycled. Annual production of plastic worldwide is approximately 350 million tons, of which approximately 10% ends up being recycled, 12% is incinerated, and the remainder (78%) accumulates in landfills or the natural environment, where it takes nearly 500-1,000 years to degrade. Plastic production is expected to double by 2030 and triple by 2050. Recycling processes depend on accurate material characterization and sorting.

Vibrational spectroscopy is one approach to characterize the interaction of matter with light, and affords a technique for identifying a material by a unique pattern of spectral features. Covalent bonds between constituent atoms in a molecule absorb infrared (IR) radiation at characteristic frequencies. The different vibrations of the different functional groups in the molecule give rise to spectral features, such as peaks and bands, of differing intensity. Another factor that determines the feature intensity in infrared spectra is the concentration of molecules in the sample. As a result, many materials exhibit a characteristic absorbance pattern in the infrared spectrum, which can be measured by spectroscopy and can be used to identify the material. Identification of materials by IR spectroscopy forms the foundation of many analytical techniques in materials processing, such as material sorting. For example, an unidentified material is characterized by IR radiation to generate a characteristic absorbance spectrum, which is then compared to a library of characteristic absorbance spectra for known materials to find a match. The match involves evaluating a fit across multiple features in terms of both energy and intensity. In some cases, as when intensity-calibrated instruments are used, the composition of the unidentified material can also be determined from IR spectroscopy.

Typical spectroscopic instruments are designed to provide wide-spectrum analytical characterization and are prohibitively expensive for large-scale implementation. The high cost is a major barrier to the deployment of sensors which can be used to screen the molecular composition of feedstocks and material streams in various industrial processes. Effective sensors are needed to interrogate the chemical constituents of target materials with specificity, as part of materials identification, sorting, and processing.

SUMMARY

Techniques are provided (e.g., a method, a system, non-transitory computer-readable medium storing code or instructions executable by one or more processors) for configuring sensor-detector systems to characterize vibrational spectra of molecular components incorporated in waste materials, using genetic algorithms (GA).

In particular, techniques are directed to generating an implementation configuration of a light source array, to be implemented as part of a material characterization system. The techniques include one or more AI implementations including, but not limited to, GAs. The approaches described herein permit identifying light source configurations with high spectroscopic specificity for a target material or a target material classification. The GAs include a machine learning model, such as a classifier. The classifier may be trained to evaluate candidate light source configurations for material specificity. For example the classifier may determine the suitability of a the candidate light source configuration to interrogate one or more spectral features included in spectroscopic data for the target material.

In some embodiments, a method is provided for selecting a spectroscopic sensor light source configuration. The method includes obtaining, by a computer system, a light source dataset describing a plurality of light sources and a spectroscopic dataset describing a plurality of materials. The method includes initializing, by the computer system, a genetic algorithm with an initial generation of solutions, an individual solution of the initial generation of solutions comprising a subset of light sources of the plurality of light sources. The method includes selecting, by the computer system using the genetic algorithm, a first individual solution and a second individual solution from the initial generation of solutions, the first and second individual solutions respectively described by a first chromosome encoding and a second chromosome encoding. The method includes generating, by the computer system using the genetic algorithm, a new individual solution from the first and second individual solutions by combining the first chromosome encoding and the second chromosome encoding. The method includes evaluating, by the computer system using the genetic algorithm, a specificity of the new individual solution to a target material of the plurality of materials. The method includes, in accordance with the specificity of the new individual solution to the target material surpassing a specificity of the first individual solution to the target material or a specificity of the second individual solution to the target material: adding, by the computer system using the genetic algorithm, the new individual solution to a new generation of solutions. The method includes, populating, by the computer system using the genetic algorithm, the new generation of solutions with a plurality of new individual solutions. The method includes generating, by the computer system using the genetic algorithm, one or more subsequent generations of solutions by iterating the genetic algorithm. The method includes selecting, by the computer system using the genetic algorithm, one or more implementation individual solutions from a final generation of the one or more subsequent generations, the one or more implementation individual solutions exhibiting a threshold specificity to the target material. The method also includes outputting, by the computer system, the one or more implementation individual solutions, wherein an implementation individual solution of the one or more implementation individual solutions comprises a spectroscopic sensor light source configuration.

In some embodiments, evaluating the new individual solution includes inputting the new individual solution into a classifier model implemented in an artificial neural network. Evaluating the new individual solution includes inputting the spectroscopic dataset into the classifier model, the spectroscopic dataset comprising a plurality of spectra from a plurality of material classifications. Evaluating the new individual solution also includes evaluating, for the new individual solution using the classifier model, a lowest intergroup distance between a first material classification comprising the target material and a second material classification excluding the target material. The lowest intergroup distance describes the specificity of the new individual solution to the target material relative to one or more other materials.

In some embodiments, evaluating the specificity of the new individual solution to the target material includes generating a plurality of projections by projecting the plurality of spectra onto the subset of light sources making up the new individual solution. Evaluating the specificity of the new individual solution to the target material includes generating a plurality of accuracy values using the plurality of projections. Evaluating the specificity of the new individual solution to the target material includes mapping the plurality of accuracy values onto a feature space. Evaluating the specificity of the new individual solution to the target material includes identifying one or more clusters of accuracy values in the feature space. Evaluating the specificity of the new individual solution to the target material also includes evaluating a plurality of intergroup distances between the one or more clusters of accuracy values.

In some embodiments, the spectroscopic dataset includes a plurality of FTIR absorbance spectra for a plurality of materials categorized into the plurality of material classifications. The subset of light sources may include ten light sources, respectively described by a central wavelength and a wavelength range. Evaluating, by the computer system, the first and second individual solutions may be based in part on an output of a fitness function, the fitness function indicative of the specificity of the first and second individual solutions to the target material. Generating the new individual solution may include deduplicating the subset of light sources by removing duplicate light sources contributed to the new individual solution from both the first individual solution and the second individual solution. The method may also include retaining an individual solution across the one or more subsequent generations when a specificity of the individual solution to the target material exceeds a threshold. The target material may be or include a type-standard of a class of materials, a specific material within the class of materials, an additive, a contaminant, a constituent material, or a composite material.

In some embodiments, outputting the one or more implementation individual solutions includes providing the implementation individual solution to an assembly system configured to build a spectroscopic sensor light source from a spectroscopic sensor light source configuration. Outputting the one or more implementation individual solutions also includes building, according to the implementation individual solution, the spectroscopic sensor light source.

In some embodiments, outputting the one or more implementation individual solutions includes configuring a spectroscopic sensor light source of a material screening system according to an implementation individual solution of the one or more implementation individual solutions. Outputting the one or more implementation individual solutions includes screening a waste material stream, using the spectroscopic sensor light source, for the target material. Outputting the one or more implementation individual solutions also includes selecting the target material from the waste material stream.

In some embodiments, a method is provided for configuring a spectroscopic sensor light source cascade. The method includes obtaining, by a computer system, a light source dataset describing a plurality of light sources and a spectroscopic dataset describing a plurality of materials. The method includes identifying a primary target material and a secondary target material of the plurality of materials. The method includes generating, by the computer system using a first genetic algorithm, a primary implementation individual solution exhibiting a threshold specificity to the primary target material and generating, by the computer system using a second genetic algorithm, a secondary implementation individual solution exhibiting a threshold specificity to the secondary target material. The method also includes outputting, by the computer system, the primary implementation individual solution and the secondary implementation individual solution. The primary target material includes a first material class and the secondary target material includes a first member of the first material class. The primary implementation individual solution is generated to differentiate the first material class from a second material class. The secondary implementation individual solution is generated to differentiate the first member of the first material class from a second member of the first material class.

In some embodiments, generating the primary implementation individual solution includes identifying one or more bands of interest from the spectroscopic dataset associated with the primary target material. Generating the primary implementation individual solution includes initializing, by the computer system, the first genetic algorithm with an initial generation of solutions, an individual solution of the initial generation of solutions comprising a subset of light sources of the plurality of light sources. Generating the primary implementation individual solution includes selecting, by the computer system using the first genetic algorithm, a first individual solution and a second individual solution from the initial generation of solutions, the first and second individual solutions respectively described by a first chromosome encoding and a second chromosome encoding. Generating the primary implementation individual solution includes generating, by the computer system using the first genetic algorithm, a new individual solution from the first and second individual solutions by combining the first chromosome encoding and the second chromosome encoding. Generating the primary implementation individual solution includes evaluating, by the computer system using the first genetic algorithm, a specificity of the new individual solution to the primary target material based in part on the one or more bands of interest. generating the primary implementation individual solution includes, in accordance with the specificity of the new individual solution to the primary target material surpassing a specificity of the first individual solution to the target material or a specificity of the second individual solution to the primary target material: adding, by the computer system using the first genetic algorithm, the new individual solution to a new generation of solutions. Generating the primary implementation individual solution includes populating, by the computer system using the first genetic algorithm, the new generation of solutions with a plurality of new individual solutions. Generating the primary implementation individual solution includes generating, by the computer system using the first genetic algorithm, one or more subsequent generations of solutions by iterating the first genetic algorithm. Generating the primary implementation individual solution also includes selecting, by the computer system using the first genetic algorithm, the primary implementation individual solution from a final generation of the one or more subsequent generations, the primary implementation individual solution exhibiting a threshold specificity to the primary target material.

In some embodiments, evaluating the specificity of the new individual solution to the primary target material includes generating a plurality of projections by projecting a plurality of spectra of the spectroscopic dataset onto a subset of light sources of plurality of light sources making up the new individual solution. Evaluating the specificity of the new individual solution to the primary target material includes generating a plurality of accuracy values using the plurality of projections. Evaluating the specificity of the new individual solution to the primary target material includes mapping the plurality of accuracy values onto a feature space. Evaluating the specificity of the new individual solution to the primary target material includes identifying one or more clusters of accuracy values in the feature space. Evaluating the specificity of the new individual solution to the primary target material includes evaluating a plurality of intergroup distances between the one or more clusters of accuracy values. Evaluating the specificity of the new individual solution to the primary target material also includes evaluating a lowest intergroup distance from the plurality of intergroup distances, where the lowest intergroup distance describes the specificity of the new individual solution to the primary target material relative to one or more other materials.

In some embodiments, a system is provided that includes one or more data processors and a non-transitory computer readable storage medium containing instructions which, when executed on the one or more data processors, cause the one or more data processors to perform part or all of one or more methods disclosed herein. In some embodiments, the second genetic algorithm is the first genetic algorithm.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the claims. Thus, it should be understood that although the present disclosure includes various embodiments and optional features, modification and variation of the concepts herein disclosed may be resorted to by those skilled in the art, and that such modifications and variations are considered to be within the scope of this disclosure as defined by the appended claims.

Figure 1:
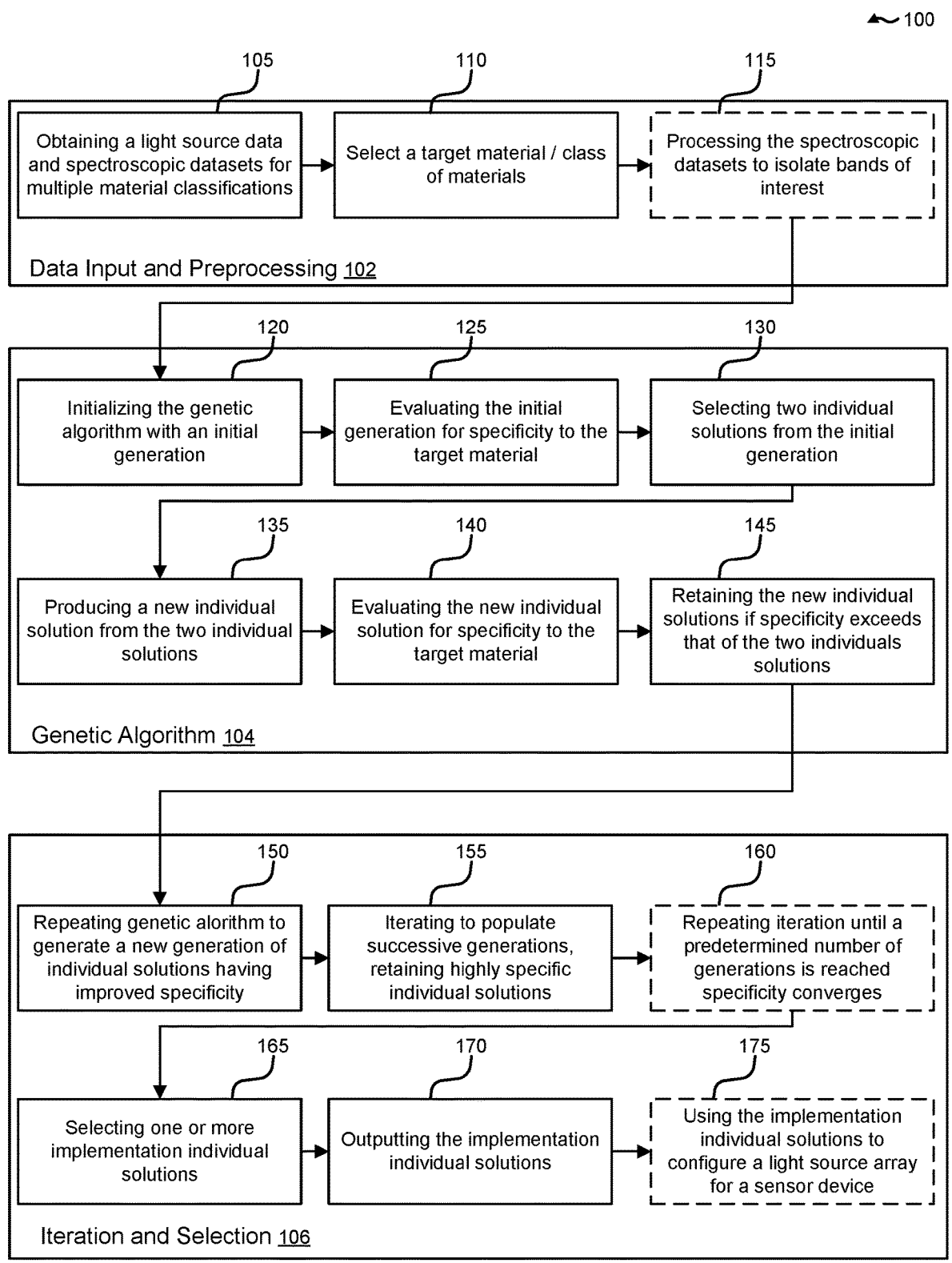
FIG. 1 illustrates an example workflow for configuring an light source array to identify a target material, according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual solution embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. INTRODUCTION

Mechanical recycling, which describes physical processing to reuse or reform waste materials, is limited in its applicability to mixed, composite, and contaminated waste streams. For example, mechanical recycling typically employs mechanical separation and reformation processes that are insensitive to chemical contaminants and may be unable to modify the chemical structure of waste material, which may exclude some chemical structures or impure materials from recycling processes. Chemical recycling may resolve the limitations of mechanical recycling by breaking the chemical bonds of waste materials into smaller molecules. For example, in the case of polymeric materials, chemical recycling may provide an avenue to recover oligomers, monomers, or even basic molecules from a plastic waste feedstock. In the case of polymers, chemical recycling processes may include operations to depolymerize and dissociate the chemical makeup of a complex plastic product, such that by-products can be up-cycled into feedstocks for new materials.

While example embodiments described herein center on polymeric materials or organic chemical materials, these are meant as non-limiting, illustrative embodiments. Embodiments of the present disclosure are not limited to such materials, but rather are intended to address material processing operations for which a wide array of materials serve as potential feedstocks for a material recycling and/or up-cycling process. Such materials may include, but are not limited to, metals, glass, bio-polymers such as ligno-cellulosic materials, visco-elastic materials, minerals such as rare earth containing materials, as well as complex composite materials or devices.

Elements of chemical recycling may permit a material to be repeatedly dissociated into primary feedstock materials. In this way, rather than being limited by chemical structure and material integrity to a limited number of physical processes, as in mechanical recycling, the products of chemical recycling may include basic monomers (ethylene, acrylic acid, lactic acid, etc.), feedstock gases (carbon monoxide, methane, ethane, etc.), or elemental materials (sulfur, carbon, etc.). As such, chemical recycling may permit improved implementation of reuse and recycling strategies based on chemical conversion of a waste material.

Successful implementation of chemical recycling may rely at least in part on accurate identification of waste feedstocks by spectroscopic characterization. Vibrational spectroscopy is one approach to characterizing the interaction of matter with light, and affords a technique for identifying a material by a characteristic pattern of spectral features, such as absorbance peaks in an infrared spectrum (e.g., FTIR ATR).

Instruments for rigorous spectroscopic characterization of materials typically possess a broad spectral range and have excellent sensitivity, but are cost prohibitive, are complex to operate, and involve considerable data analysis expertise. Development of pre-configured light source arrays tailored to a specific target material, however, may allow algorithmic classification of the target material at accuracy levels equivalent to a general-purpose spectroscopic instrument. Such arrays may be constructed including multiple monochromatic light sources having a relatively limited spectral range, selected to interrogate specific spectroscopic bands in the target material. For example, an array of IR-spectrum light emitting diodes (LEDs) or laser diodes could be combined in a manner that may reduce the complexity of material characterization and the expense of implementing an identification process in a material recycling facility. Furthermore, cascaded sensors may implement a coarse-to-fine identification system to precisely identify specific additives or contaminants in a waste material without deconvolution analysis, as part of continuous material sorting operations.

As used herein, a spectrum can describe an emission spectrum or an absorbance spectrum. An emission spectrum can show radiation intensity as a function of wavelength, as generated by measuring radiation output by a radiation source. By contrast, an absorbance spectrum describes an intensity of absorption of radiation by a material as a function of energy, which can be expressed as frequency, wavelength, wavenumber, or energy, and can correspond to radiation selectively reflected or selectively transmitted by the material. In the context of chemical spectral libraries or databases, absorbance spectra can describe the characteristic pattern of spectral features for non-emissive materials.

The correct identification of waste material components is of vital importance, at least because the presence of some additives or contaminants may render a waste material unsuitable for chemical recycling. For example, halogen-containing materials, such as chlorinated or fluorinated polymers, may produce corrosive byproducts during some chemical recycling processes, which may damage or destroy chemical recycling units. Furthermore, different classes of materials, for example, different classes of polymers and plastics, may be sent to different and mutually-incompatible recycling processes. In this way, configuring an accurate, high-speed, and low cost sensor may permit improved identification of waste materials, and thus improved implementation of chemical recycling.

Genetic Algorithm (GA) approaches described herein improve recycling processes by providing accurate, specific, and scalable material characterization sensor array light sources for classification and identification of waste materials, additives, impurities, and contaminants. While broad-spectrum instruments provide detailed absorbance information for materials, analysis of materials with such instruments typically includes sample preparation procedures, analytical methods, and spectrum analysis (e.g., base-lining, deconvolution, labeling, etc.). In this way, general characterization using laboratory instruments is time consuming and uses expensive machines that provide measurements with more precision than what is needed for material sorting or screening. By contrast, the GA approaches described herein generate and select an optimized light source array configuration that is specific to a target material class (e.g., a type-standard of a class of materials), a target material, an additive material, a contaminant, a composite material, or constituent materials within a target material, using characteristic spectral databases and light source emission profile data as inputs. Light source arrays and cascaded light source arrays described herein are used in sensor systems during intake and sorting of waste materials to accurately identify real-world waste materials received at material processing facilities.

A system implementing a GA, as disclosed herein, may incorporate machine learning (ML) models as an approach to evaluating the specificity of candidate configurations, also referred to as chromosome encodings. For example, clustering techniques may permit an estimation of an intergroup distance, from which the specificity to a material classification, material, or constituent compound may be ascertained. In some cases, the ML model may include a classifier model trained to return whether a candidate is accurate for differentiating a target material.

One illustrative embodiment of the present disclosure is directed to a system that includes one or more data processors and a non-transitory computer readable storage medium containing instructions which, when executed on the one or more data processors, cause the one or more data processors to perform actions including obtaining light source data and spectroscopic data for materials. Characteristic spectra, such as FTIR absorbance spectra for arbitrary waste materials may be obtained from a database of chemical data. The characteristic spectra may be categorized, for example by inclusion of metadata, into a number of material classifications. Similarly, light source information, such as central emission wavelength and emission range information, may be obtained from an inventory of available light sources.

The actions further include initializing a genetic algorithm with an initial generation of solutions, where an individual solution is described as a chromosome encoding including a number of light sources included in the light source data; selecting a first individual solution and a second individual solution from the initial generation, where the first and second individual solutions serve as parents; generating a new individual solution, also referred to as a child, from the first and second individual solutions by combining the chromosome encodings of the two parents; evaluating the child using the spectroscopic dataset to determine a specificity of the child; in accordance with the specificity of the new individual solution to a target material surpassing that of the parents: adding, by the computer system, the new individual solution to a new generation of solutions; populating the new generation of solutions with a plurality of additional children to equal a number of individual solutions in the initial generation; iterating the genetic algorithm to generate improved generations; identifying one or more implementation individual solutions; and outputting the one or more implementation individual solutions for use in a chemical recycling process.

Another illustrative embodiment of the present disclosure is directed to a system that includes one or more data processors and a non-transitory computer readable storage medium containing instructions which, when executed on the one or more data processors, cause the one or more data processors to perform actions including developing cascaded light source configurations, such that a primary light source is optimized to differentiate a primary target material from other materials by class, a secondary light source is optimized to differentiate a secondary target material from other materials within a class, and a tertiary light source is optimized to differentiate a tertiary target material from other materials that contain contaminants or other impurities that are to be excluded from further processing.

Advantageously, these techniques can overcome a limitation of conventional recycling methods that typically are devised to process relatively pure waste streams, with minimal contaminants. The techniques described herein further improve recycling processes by developing scalable sensor systems, which are deployable in a short time and at greatly reduced cost, relative to analytical instruments. As such, GA-based configuration and selection approaches permit the development of characterization systems for screening of waste materials for improved sorting, process design, and process optimization techniques in chemical recycling networks.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. As used herein, when an action is "based on" something, this means the action is based at least in part on at least a part of the something.

II. TECHNIQUES FOR CONFIGURING LIGHT SOURCE ARRAYS

Figure 2:
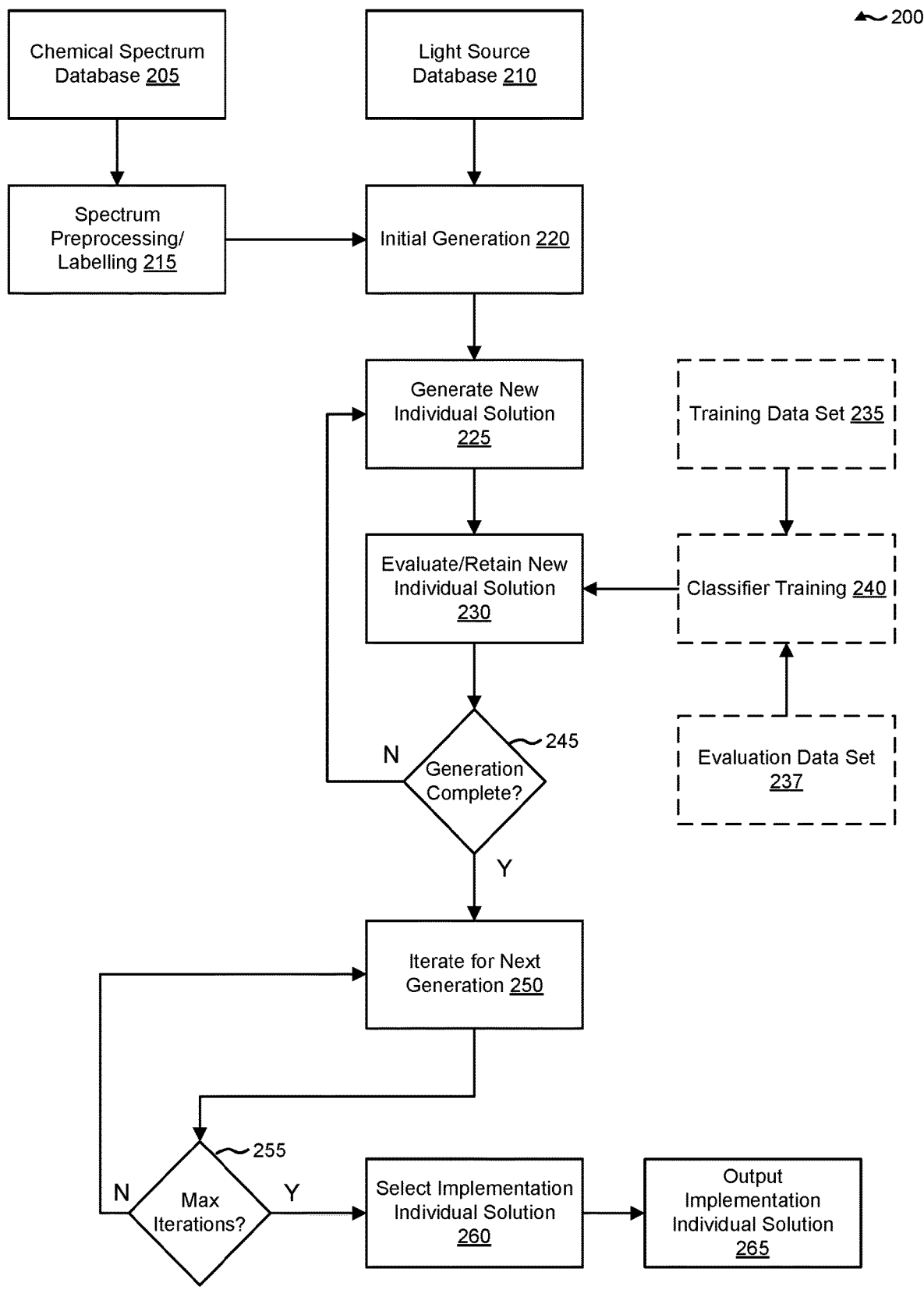
FIG. 2 illustrates an example workflow for a genetic algorithm configured to generate a light source array specific to a target material, according to various embodiments.
Figure 5:
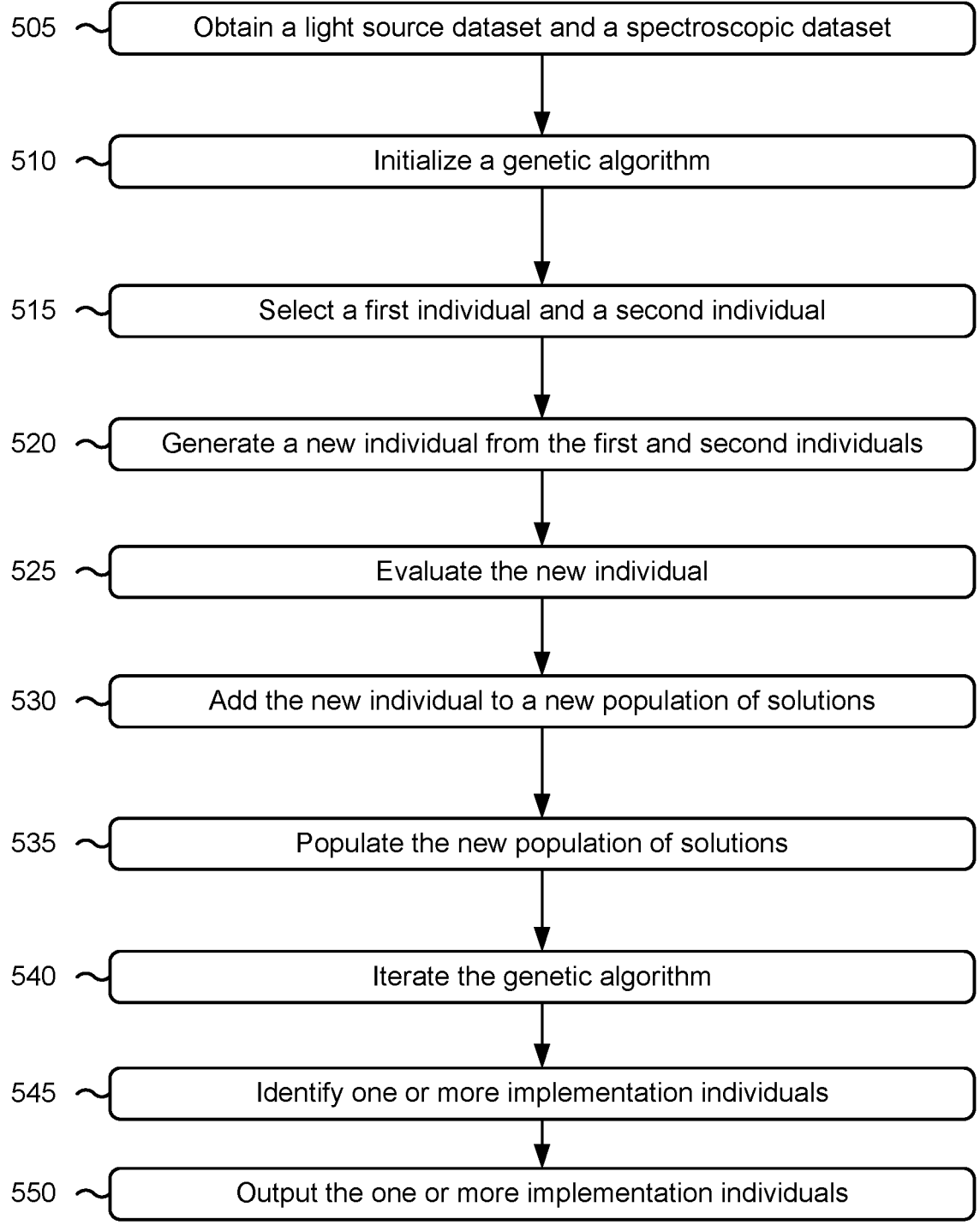
FIG. 5 illustrates an example flow describing a method for generating a light source array for identifying a target material, according to various embodiments.

FIGS. 1, 2 and 5 depict simplified flowcharts depicting processing performed for configuring an light source array to identify a target material according to various embodiments. The steps of FIGS. 1, 2, and 5 may be implemented in the system environments of FIG. 6, for example. As noted herein, the flowcharts of FIGS. 1, 2, and 5 illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 1 illustrates an example workflow 100 for configuring a light source array to identify a target material, according to various embodiments. As shown in FIG. 1, the workflow 100 is subdivided into sub-processes for data input and preprocessing 102, genetic algorithm 104, and iteration and selection 106 of a spectroscopic sensor light source configuration. The data input and preprocessing 102 includes various steps to obtain light source and spectroscopic datasets and identify a characteristic spectrum of a target material, to be used to populate a generation of individual solution configurations. As part of the data input and preprocessing 102, at step 105, light source data and spectroscopic data for multiple material classifications are obtained by a computing device. Light source data may describe light emission properties of a number of different light sources including, but not limited to, monochromatic light emitting diodes (LEDs), tunable lasers, glow discharge lamps, broad-spectrum emitters, or other light sources that generate radiation in a wavelength applicable to vibrational spectroscopy. In the context of the workflow 100, light emission properties refer to a central wavelength of a light source, a wavelength range over which the light source emits radiation, as well as other physical properties including, but not limited to, tunability, polarization, fluence, or intensity. The light source data may be obtained by the computing device from private or public database sources, such as manufacturer calibration data or public government data such as those prepared by the NIST. Alternatively, the light source data may be generated by aggregating published data in scientific literature or by performing intensity calibrated spectrometry to generated characteristic emission spectra for a library of light sources. In such cases, obtaining the light source data includes accessing a database of characteristic emission spectra for the library of light sources.

In some embodiments, the spectroscopic data are obtained by the computing device from one or more private or public database sources, such as PubChem, ChemSpider, Reaxys, or the NIST. The private or public database sources may include a centralized, standards compliant, data repository for spectroscopy data, including chemical identifiers or identification numbers, such as CAS numbers, chemical structures according to various structural representation formats, and supporting spectral evidence. Spectral evidence may include standard, uncalibrated, or intensity-calibrated vibrational spectra, such as FTIR-ATR spectra collected from pure-control samples or standard composites. Detailed descriptions of both spectroscopic data and light source data are provided in reference to FIGS. 3A and 3B, respectively. Spectroscopic data may include multiple materials categorized within material classifications, for example, based on monomer unit structure, side-chain chemistry, or other characteristic chemical features that are relevant to chemical recycling processes.

For example, the presence of halogen side chains in a polymer waste material may form corrosive byproducts during chemical recycling. In this way, a polymer class, such as poly-vinyl polymers, may be screened not by monomer structure, but rather by side-chain chemistry. As an example, where polyvinyl chloride produces chlorine gas and other corrosive chemicals in some chemical recycling processes, polyvinyl acetate, which does not contain halogen atoms, will not generate corrosive byproducts.

At step 110, a target material is selected. The target material may be designated externally, for example, by the computer system receiving an input of a material identifier. Alternatively, the target material may be selected autonomously (e.g., without human interaction), as part of a machine process to configure an array of light sources. As previously described, databases of spectroscopic data often identify materials using chemical identifiers or identification numbers, such as CAS numbers. In this way, spectroscopic data the target material can be accessed from the spectroscopic dataset using the chemical identifier. As an illustrative example, polyethylene terephthalate (PET), which is a common plastic used for disposable bottles, polyester fabric, Mylar, and other products, is identified by a CAS number 25038-59-9. The CAS number is also included as metadata in spectral databases maintained by PubChem and other sources. As such, the CAS number may serve as a search key to identify a spectrum of the target material. In another example, a library of spectroscopic data is collected by the computer system and stored locally, such that a spectrum for the target material is retrieved upon receipt of metadata identifying the target material, such as a CAS number.

The operations at step 110 include selecting a target class of materials within which to differentiate the target material. For example, where a target material is a polymer, such as PET, the class of materials includes all polymers types, as described by characteristic spectroscopic data. As such, spectroscopic data for other material classes, such as glass, metal, biopolymers, are excluded. Polymeric materials are classified in several ways, but in the context of material recycling, a resin identification code (MC) is a common classification approach. In this way, the spectroscopic dataset is selected for multiple RIC classes, to be used in evaluation operations described in more detail in reference to step 125 and step 140, as well as in reference to FIG. 2.

At step 115, the workflow 100 may optionally include processing the spectroscopic datasets to isolate bands of interest. Bands of interest describe wavelength bands in spectroscopic data that contain characteristic spectral features of a material. For vibrational spectra, the characteristic spectral features include, but are not limited to peaks or bands that result from the interaction of covalently bonded atoms in the material with radiation in the IR range. While most materials, such as polymers or other organic chemicals, produce vibrational spectra including many characteristic spectral features, some features or groups of features are attributable to a class of materials and others to a specific material belonging to the class. In some cases, characteristic spectral features may also be attributable to the structure of a material. In the case of polymeric materials, for example, monomer chemical structure strongly influences the characteristic spectrum of the overall material. As such, a class of polymers including variants on a basic polymer backbone, such as polyethylene, polypropylene, polystyrene, or polyvinyl, may be identified by the characteristic spectral features of the monomer. Structures such as sidechains, functional groups, or copolymers, may add features or modify the features produced by the polymer backbone. In this way, specific spectral features may distinguish a general class of materials, or a specific material from the class, and be used to screen materials. Furthermore, variation of the characteristic spectral features may permit screening of a material based on structural features within a specific material, as well as within a class of materials.

As an illustrative example, cross-linked polyethylene (XLPE) is a thermosetting resin with three types of cross-linking: peroxide cross-linking, radiation cross-linking, and silane cross-linking. The polymer can be effectively recycled when the cross-linking points are decomposed chemically, but is not directly mechanically recycled, due in part to its phase-transition properties. Low density polyethylene (LDPE), by contrast, can be recycled mechanically because it presents different thermal properties that allow it to be melted and reformed without chemical decomposition. In this example, spectral features included in spectroscopic data for XLPE include features that identify the monomer chemistry, as well as structure. In particular, cross-linking extent is detectable in vibrational spectra, at least because spectra for LDPE and XLPE differ in features attributable to carbon-hydrogen covalent bonds. Furthermore, where some features are shared between LDPE and XLPE spectra, relative intensity of shared features may differ between the two materials. The example of LDPE and XLPE demonstrates that two polymers of similar monomer chemistry, may be treated differently by chemical recycling processors and may be detected and screened by their characteristic spectra.

Illustrated as part of the genetic algorithm (GA) 104, GA approaches are used to generate a new individual solution from two parents. An individual solution is a configuration of light sources combined in an array, where the configuration of light sources includes a subset of the light sources described in the light source database of step 105. The GA 104, therefore, generates an array of light sources with characteristic emission patterns that are optimized for the target material. The subset includes a number of light sources such that the spectroscopic sensor light source array is able to differentiate the target material from other materials as part of a chemical recycling process. In this context, optimized refers in part to projection of spectroscopic features and characteristics of the target material onto the characteristic emission patterns of the individual solution, as described in more detail in reference to FIGS. 4A-4B.

GAs are a class of computational models that implement evolutionary mechanisms to generate candidate solutions to optimization problems. GAs develop an optimized individual solution by generating successive generations of candidate solutions, progressively improved with respect to a fitness function. The improvement of each successive generation is effected by iteratively generating and selecting individual solutions from each generation to populate the following generation. As such, the GA 104 incorporates several processes including, but not limited to, chromosome encoding, a function to generate new solutions, fitness evaluation, selection mechanisms, genetic operators, and convergence/termination criteria.

In the context of the present disclosure, a chromosome encoding may describe binary and non-binary approaches to encoding a light source array in vector form. For example, the chromosome encoding may be a vector of binary values, where a value in the vector is true if a corresponding light source is included in the individual solution and is false if the light source is excluded from the individual solution, thereby defining the subset of light sources. In this way, each chromosome encoding may be a fixed-length binary vector with a predetermined size equal to the number of light sources included in the light source dataset obtained in step 105. Alternatively, the chromosome encoding may be a vector of integer values, floating point values, or graphical data. For example, the chromosome encoding may be a fixed-length integer vector of a pre-determined size corresponding to a number of light sources included in the subset, where particular light sources are identified by integer values encoding the identity of the light source. Similarly, the chromosome encoding may be a floating-point vector, where the light sources are identified by a rational number. In the example of the binary encoding, to accommodate a configuration that includes a predetermined number of light sources, the function to generate new solutions may impose rules on candidate solutions, such that each candidate solution includes the same number of light sources, the composition of which differs across candidates in a given generation.

In step 120, the genetic algorithm is initialized. The initial generation may be generated by randomized population. In some embodiments, generating an initial candidate solution includes randomly selecting the pre-defined number of light sources from the light source database. The initial generation would therefore include a population of candidate solutions each having a random combination of light sources totaling the pre-defined number. The pre-defined number may include, but is not limited to, five light sources, six light sources, seven light sources, eight light sources, nine light sources, ten light sources, or more light sources, corresponding to a number of characteristic spectral features that provide a match to a target material, as described in more detail in reference to FIGS. 3A-4B, below. Randomly populating the initial generation in this way permits the GA 104 to evolve candidate solutions from a larger number of possible combinations, and therefore improves the ability of the GA 104 to evolve an optimal configuration. Where the optimal configuration interrogates a material at a number of characteristic spectral features, however, the light source database may include relatively few light sources that project onto the characteristic spectral features. As such, a fully randomized initial generation may converge to an optimized generation over a relatively large number of generations.

In some cases, populating the initial generation may include generating a pseudo-randomized population. For example, the bands of interest, discussed in reference to the step 115, identify wavelength regions of an infrared spectrum containing characteristic spectral features attributable to material classes, members of a given class, specific bonds, or bond types (e.g., aromaticity) within materials. The GA 104 may generate a pseudo-randomized light source configuration to identify a specific material by randomly selecting a pre-defined number of light sources that emit light within one or more bands of interest for the specific material. The pseudo-random approach can improve performance of the GA 104, for example, by providing an initial generation that does not include light sources that emit light outside the wavelength regions containing characteristic features of the material. This may be implemented by filtering techniques, as described in more detail in reference to FIG. 2, below. As a further advantage, the pseudo-random approach reduces the effective size of the light source database by excluding light sources that emit outside the identified bands of interest. Reducing the effective size of the light source database limits the number of possible combinations for candidate solutions and reduces the number of generations for convergence to an optimized individual solution.

The size of the initial generation may be maintained across successive generations on the order of tens of individual solutions, on the order of hundreds of individual solutions, on the order of thousands of individual solutions, or more. For each individual solution of the initial generation, a specificity to the target material is evaluated at step 125. The fitness function of the GA 104 evaluates the specificity as an example of a figure of merit that is used to describe how well the candidate solution differentiates the target material from other materials. The fitness function may include, but is not limited to, scalar-valued functions implemented using procedural rule-based procedures, object models, or machine learning models, such as classifier models implemented in an artificial neural network and having been trained to evaluate individual solutions for accuracy.

In some embodiments, an evaluation of the specificity is determined by projection of the characteristic spectral features of the target material onto the light sources making up each individual solution. Both the proximity of a main emission wavelength and a spread parameter, such as the full width at the half-maximum, may be included to estimate the ability of the candidate solution to emit infrared radiation at wavelengths overlapping the characteristic features of the target material, as described in more detail in reference to FIG. 4. A classifier model may be trained to input a candidate solution and evaluate its accuracy. The training may include supervised, unsupervised, or adversarial training approaches. For example, a classifier may be trained to evaluate the specificity of candidate solutions by an adversarial network, where the classifier is trained to predict whether a candidate solution will identify a target material with specificity relative to a different material, material class, or other characteristic aspect of the material.

In an illustrative example, described in more detail in context to FIG. 2, below. The classifier is trained by evaluating an $F_1$-score of a logistic regression applied to differentiate a target material from a class of other materials. In this example, the training includes transforming the set of spectroscopic data for a class of materials, such as polymers, using the constituent light sources of an individual solution as described in the chromosome encoding of the individual solution. The transformed spectroscopic dataset is split into a training subset and an evaluation subset, each including data from multiple material sub-classes, described by resin identification codes. The training data are then used to train the classifier. The $F_1$-score is derived using the evaluation data, which is then outputted by the classifier as the specificity of the individual solution to the target material.

In some embodiments, the fitness function may describe a specificity in terms of a lowest intergroup distance. In the context of the workflow 100, the lowest intergroup distance refers to the specificity of the individual solution to the target material, as compared to a similar material class, a similar material, or a similar additive/contaminant. As an example of material class screening, the GA 104 may generate candidate solutions for a light source configuration to screen polyethylene polymers out of waste containing polyethylene polymers, poly-vinyl polymers, polystyrene polymers, and poly-lactic acid polymers. As such, the fitness function may evaluate the specificity for each individual solution against a number of characteristic absorbance spectra for materials from each group, from which the specificity data are mapped to a feature space and clustered in that space according to metadata identifiers of the spectra, and distances between the clusters are calculated. The feature space may be defined in such a way that clusters are best separated, thereby facilitating the estimation of the intergroup distances. The lowest intergroup distance describes the distance between the clustered data points for polyethylene and the clustered data points for the other material classes. The lowest intergroup distance for each individual solution, therefore, describes the specificity of the individual solution to polyethylene over the nearest other material class. In this way, the individual solution having the highest intergroup distance is the most specific to the target material.

Material class sorting is one possible approach to evaluating individual solutions within a generation, but other approaches are also possible. For example, as described in reference to FIG. 4A-4B, individual solutions may be evaluated by estimating an accuracy parameter for a specific target material, rather than a material class. The lowest intergroup distance relies on a sufficiently precise definition of groups within a material class, but where the target material is a specific material, for example a chlorinated polymer, the specificity may be defined relative to non-chlorinated polymers, such as polyethylene vs polyvinyl chloride, which have identical monomer chemistry with the exception of a single hydrogen atom being substituted for a chlorine atom. As such, intergroup distance is but one possible approach to evaluating the specificity of an individual solution to the target material or the ability of the individual solution to differentiate two target materials from each other, as in sorting one from another.

At step 130, two individual solutions, also referred to as parents, are selected from the initial generation populated at step 120. The selection may be random, but may also be made in reference to the specificity of the initial generation to the target material. For example, the initial population may be binned according to specificity, such as by percentile or other criterion, and the two individual solutions may be selected from different bins. Advantageously, random selection may provide increased variability in subsequent combination and mutation steps, which may benefit the overall performance of the GA 104 for generating and selecting an optimized individual solution.

At step 135, the chromosome encodings of the two individual solutions are combined, subject to constraints of the GA 104, to produce a new individual solution, also referred to as a child. The GA 104 may apply various approaches to combining the chromosome encodings. Stochastic methods may include, but are not limited to genetic operators such as crossover. By contrast, cloning, by which the new individual solution contains an exact copy of one, but not both, parents, may permit the population to retain highly specific individual solutions in the new generation. In some embodiments, the approaches to crossover may include, but are not limited to, single-point crossover, two-point or k-point crossover, uniform crossover, or ordered crossover.

Ordered crossover includes constraints on the portion or the type of crossover implemented at step 135. For example, where a candidate solution is a vector of integers representing light sources, the two individual solutions may be combined by randomly selecting approximately half of the entries from each individual solution and removing any duplicate entries (e.g., deduplicating the light sources of the new individual solution). The resulting vector, when including fewer than the complete number of light sources, may be completed by randomly selecting a light source from the database, or from the parent individual solutions. In another example, ordered crossover may include selecting longer wavelength light-sources from one parent, and shorter wavelength light sources from the second parent. In another example, a minimum wavelength spacing may be imposed as a constraint, such that the child excludes not only duplicate light sources, but also light sources that overlap by a sufficient extent. Such cases may occur when the light source database includes multiple light sources that provide alternative coverage of similar wavelength ranges, for example, to accommodate market or other logistical conditions, such as the availability of specific light sources.

Producing the new individual solution, as part of step 135, may include mutating the chromosome encoding of the new individual solution. Mutation alters one or more gene values in the chromosome encoding from its initial state. Mutation may include a pre-defined mutation probability that determines whether a gene value will be altered by the GA 104. Mutation adds further variability into the evolutionary process simulated by the GA 104 and can introduce diversity into the population. Mutation operators allow the GA 104 to avoid local minima in a fitness landscape by preventing the population of chromosome encodings from becoming too similar to each other. Exceeding chromosomal similarity within a population risks a premature convergence to a false optimum individual solution, instead of converging to the global optimum individual solution. Coupled with retention of highly specific individual solutions, the GA 104 may implement mutation to weight the population toward the highest fitness without overly emphasizing convergence. In some embodiments, the mutation operator generates a randomness variable for each gene value in a chromosome encoding that determines whether the gene value will mutate, also referred to as single point mutation. Alternatively, the mutation operator may implement approaches including, but not limited to, inversion and floating point mutation. Mutation operators may include, but are not limited to, bit string mutation, boundary, flip bit, Gaussian, uniform, non-uniform, or shrink operators.

Once generated, the new individual solution is evaluated for specificity to the target material at step 140. The evaluation, as in step 125, applies the fitness function, such as projecting the characteristic spectrum of the target material onto the new individual solution, to generate a figure of merit describing the specificity, which may be an accuracy percentage or other specificity criterion. At step 145, the specificity is then compared to the corresponding value of the two parent individual solutions, such that the new individual solution, the child, is retained and included in a new generation of individual solutions if its specificity exceeds that of the parents. In some embodiments, the child is retained only if the specificity exceeds both parents.

Alternatively, the child may be retained if the specificity exceeds at least one of the parents.

The workflow 100 includes, as part of the iteration and selection 106 process, repeating the GA 104 to generate a new generation of individual solutions, weighted toward fitter individual solutions, and iterating the process of populating new generations until the GA 104 outputs a generation including an individual solution approaching the global optimum. At step 150, the GA 104 repeats the steps 130-145 of selecting two parent individual solutions from the initial generation, producing a new child individual solution from the parents, evaluating the child for specificity to the target material, comparing the child to the parents, and including the child in the new generation if its specificity exceeds that of the parents. As part of step 150, the GA may populate the new generation with a number of individual solutions equal to the size of the initial population. In subsequent steps of the iteration and selection 106 process, the GA 104 may retain elite individual solutions that would otherwise be eliminated. Elite, in this context, describes individual solutions characterized by a relatively high specificity to the target material. For example, a specificity threshold may be defined above which an individual solution is classified as "elite." Since two highly specific parents are more likely than two non-specific parents to produce a highly specific child, especially when crossover implements a single point crossover and mutation is improbable, the retention criteria applied by the GA 104 may tend to replace highly specific parents with marginally more specific children.

As such, at step 155, the GA 104 iterates the process of steps 130-150 of populating a subsequent generation of individual solutions and retains elite individual solutions to promote faster convergence and to reduce the computational resource demand of each successive generation. To that end, in the context of the GA 104, the workflow 100 may include generating a list of retained individual solutions by tracking the fitness function values determined as part of populating each subsequent generation. For example, the GA 104 may generate an array of retained individual solutions ranked by specificity, such as an accuracy percentage for the target material or a minimum intergroup distance, that is updated each time a child is generated for which the specificity falls within the range already covered by the list. The array may include the identifier of the individual solution or the entire encoding of the individual solution and the specificity, such that the array is sorted according to the specificity of each retained individual solution. For example, in a generation including 256 individual solutions, 64 individual solutions that have a specificity to the target material exceeding a threshold may be retained from generation to generation. Similarly, for a generation including 1024 individual solutions, as many as 256 individual solutions may be retained.

With each subsequent generation, the number of repeated iterations of the GA 104 increases, at least in part because the accuracy and specificity of the population will tend to approach the maximum. In light of the retention criteria being based on improved specificity with respect to the parent individual solutions, the number of candidate solutions that are generated to retain a full population increases as the probability that a child individual solution will exceed the specificity of its parents decreases. To that end, the number of iterations at step 155 of the workflow 100 may be limited to a maximum number of iterations before the GA 104 is terminated. Imposition of a limit to the number of iterations prevents the GA 104 from hanging, and may also limit unnecessary computer resource usage for marginal improvements to specificity that will not improve the performance of sorting system incorporated into a chemical recycling process. The limit may be pre-defined or may also be an adaptive parameter that is optimized with respect to the tasks to which the GA 104 is applied. For example, for sorting one material class from another, relatively few iterations may suffice to converge to an optimum solution. By contrast, to differentiate between two target materials that are chemically similar may involve a larger number of iterations.

From the final generation, including the population of individual solutions that have been retained from multiple iterations of the GA 104, one or more implementation individual solutions are selected at step 165. For example, where the specificity of an individual solution is evaluated using the lowest intergroup distance parameter for use in differentiating two or more target materials, the implementation individual solution(s) are selected for having the highest intergroup distance in the generation. In the context of the iteration and selection 106 process, the retention criteria implemented as part of steps 150-155 for populating successive generations and retaining elite individual solutions across generations provides the individual solution having the highest specificity and, as such, the individual solution nearest to the global optimum.

Once selected, at step 170 the implementation individual solution is output to systems for further use in configuring light sources in a sorting system of a chemical recycling process, such as a material screening system. For example, the implementation individual solution may be mapped to a configuration form as a list of light-sources rather than a vector encoding. The configuration may be stored in a data store, output to an external system, an assembly system, or sent to a rapid fabrication system as part of a manufacturing process to build light sources for use in chemical recycling. For example, at step 175, the implementation individual solution is output to a reconfigurable LED array at a material recycling facility, which activates corresponding light sources that are included in the implementation individual solution. While in that configuration, the LED array will provide an optimized source of infrared radiation to differentiate the target material from other materials, such as, for example, to sort a waste material stream. As another example, the implementation individual solution is output to a dynamic light source incorporating tunable lasers in the infrared range. As another example, the implementation individual solution is output to a rapid prototyping machine configured to assemble a light source according to the configuration of the implementation individual solution.

In some embodiments, the workflow 100 is applied to develop cascaded light source configurations. A cascaded light source configuration describes a series of light source arrays that are optimized to differentiate materials at multiple levels such that a primary light source is optimized to differentiate materials by classification, a secondary light source is optimized to differentiate materials within a classification, and a third light source is optimized to exclude contaminants from the input stream. A cascaded light source system may be developed by selection of the spectral data used for evaluation of the specificity and, in some cases, by redefining the bands of interest for the target material. Using the different spectral data, the GA may be reapplied to target different material classes, materials within classes, or specific chemical signatures of impurities or other sorting priorities.

FIG. 2 illustrates an example workflow 200 for a genetic algorithm configured to generate a light source array specific to a target material, according to various embodiments. In some embodiments, the workflow 200 may be implemented in a computer system using the GA of the workflow 100 (e.g., GA 104 of FIG. 1) to generate, select, and output implementation individual solutions that are optimized, for example, to differentiate one target material from materials of other classes, or other materials of the same class. The individual solution elements of the workflow 200 represent systems, operations, or datasets that are included at various stages and are applied as part of completing the steps of generating, selecting, and outputting the implementation individual solution using a GA.

As a first step of the workflow 200, Spectral and light source data are obtained from a chemical spectrum database 205 and a light source database 210, respectively. The spectrum data is prepared for use by the GA by spectrum preprocessing/labelling 215 operations. The spectrum preprocessing/labelling 215 operations may include identifying the bands of interest and the target material(s), as described in more detail in reference to FIG. 1. Furthermore, the spectrum preprocessing/labelling 215 operations may include classifying spectra according to groupings for evaluating specificity in future operations. In such cases, spectra for one material class, such as polymers, are identified by metadata labels, while spectra from another material class, such as different polymers, biopolymers, glass, or other materials that produce characteristic absorbance spectra, are grouped and identified by different metadata labels.

The spectral data and light source data serve as inputs to the GA for populating an initial generation of individual solutions at block 220. The individual solutions are evaluated for specificity to the target material(s), and the GA generates a new individual solution at block 225. The new individual solution, the child, is generated from two parents according to a crossover function and a mutation function, and is evaluated at block 230 for specificity to the target material(s). The child is retained for the next generation if the specificity of the child exceeds that of the parents. Evaluating the child at block 230 may include inputting the child to a classifier implementing a machine learning model in an artificial neural network that has been trained to assess specificity or to discriminate between specific and non-specific individual solutions for the target material(s). In an example, a training data set 235 is prepared including multiple light source arrays that are configured to be specific to various materials including the target material(s). A classifier model, as a machine learning implementation, at block 240 is trained to determine an intergroup distance between the accuracy of individual solution for the target materials relative to other materials. The specificity evaluation at block 230 may, therefore, describe a specificity as a minimum intergroup distance, such that specificity is improved with higher minimum intergroup distance.

As an illustrative example, the training data set 235 is prepared from a set of characteristic spectra for a target set of materials, such as polymers. To create the training data set 235, the set of characteristic spectra are transformed using the configuration encoded in the chromosome encoding of the new individual solution generated at block 225, from which the training data set 235 and an evaluation dataset 237 are selected. The classifier, which is implemented as a logistic regression classifier in this example, is trained at block 240 to differentiate polymers by resin identifier code (MC). The MC code is a common sorting classification for material recycling facilities by which waste materials are categorized prior to input into a recycling process. In this way, training the classifier at block 240 may include deriving a statistical $F_1$-score of the classifier from the evaluation set 237. The $F_1$-score, in turn, serves as the specificity criterion of the new individual solution. In the context of the classifier of workflow 200, the $F_1$-score describes the harmonic mean of the precision and recall of the binary classification, where the precision is the ratio of correctly identified positive results to all positive results, including false positive results, and the recall is the ratio of correctly identified positive results to false negatives.

After evaluating the new individual solution at block 245 the GA will repeat the process until the generation is complete. As described in more detail in reference to FIG. 1, above, the complete generation may include elite individual solutions that are retained for having high specificity to the target material(s). With a complete generation, the GA will iterate the steps of combining parents to generate child individual solutions, evaluate the children, and retain elites, at block 250. The GA will perform a number of iterations, illustrated by the loop through block 255, until the maximum limit on the number of iterations is reached. Alternatively, the GA may apply convergence criteria such that iterations continue until the population approaches the global optimum of a fitness landscape, for example, by tracking the marginal change in an aggregate specificity value across the generations.

From the final generation, after block 255, one or more implementation individual solutions are selected at block 260. Selecting multiple implementation individual solutions provides robustness to the system by potentially avoiding supply limitations, as the genome of the implementation individual solutions describe light source configurations and the specific light sources may be unavailable at the time of configuration. As such, multiple implementation individual solutions including different subsets of the light source inventory described by the light source database permit suitable alternatives to be specified. Following selection at block 260, the implementation individual solutions are output to external systems at block 265, such that one or more of the individual solutions can be applied to sort materials at a material recycling facility, as in chemical recycling processes.

Figure 3A:
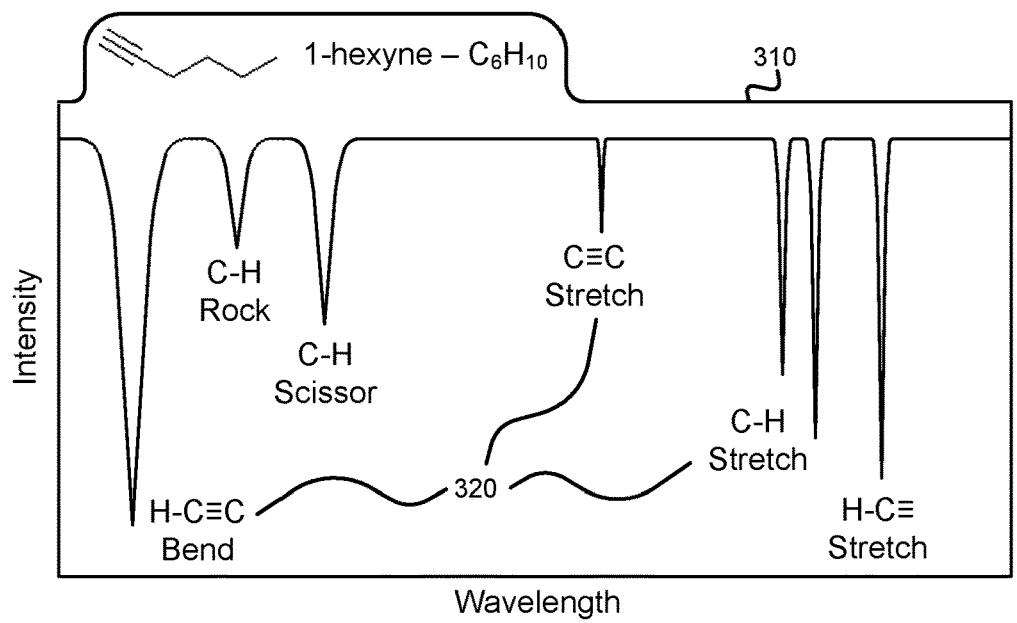
FIGS. 3A and 3B illustrate a characteristic absorbance spectrum of a chemical and an emission spectrum for configuration of light sources, according to various embodiments.
Figure 3B:
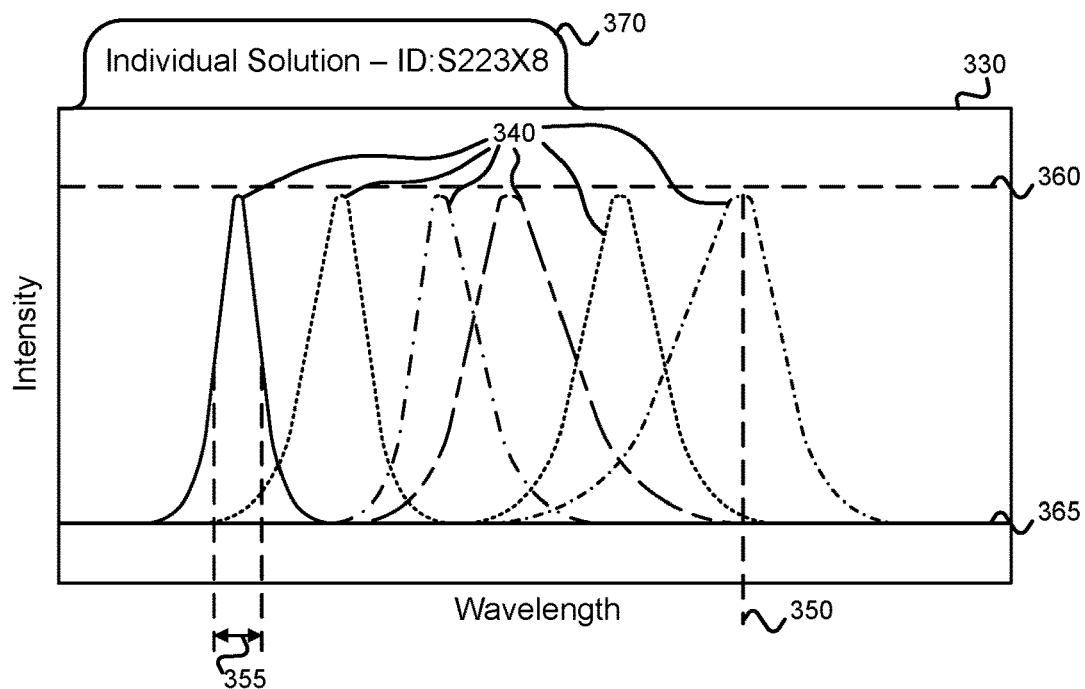

FIGS. 3A-B illustrate a characteristic absorbance spectrum 310 of a chemical and an emission spectrum 330 for configuration of light sources, according to various embodiments. In FIG. 3A, the characteristic absorbance spectrum 310 describes a simplified spectrum of 1-hexyne, a linear unsaturated hydrocarbon. The characteristic spectrum 310 of 1-hexyne is provided for simplicity, but it will be understood that the operations described in relation the characteristic spectrum 310 may be applied to more complex spectra, such as those produced by highly substituted polymers, copolymers, biopolymers, or other materials that may be received and sorted as part of chemical recycling processes. The characteristic spectrum 310 includes several characteristic spectral features 320, labeled and attributed to various covalent bonds of 1-hexyne. As illustrated, the spectral features 320 are attributed to characteristic vibrations of carbon-carbon and carbon-hydrogen bonds in the molecular structure of 1-hexyne. In this way, vibrational spectra of the target material(s) described in reference to FIGS. 1-2, above may include multiple spectral features that are attributable to covalent bonds incorporated into the molecular structure(s) of the target material(s). In the case of polymers, different polymer types are distinguishable by comparison of certain spectral features. For example, polystyrene polymers include characteristic features produced by aromatic bonds in a benzene moiety included in the monomer structure. Similarly, polyamides will include features produced by absorption of carbon-nitrogen bonds at characteristic positions in the spectra for that class of materials. Furthermore, sidechain vibrations are likely to have different energy characteristics than backbone constituents, due to constrained motion of the monomer backbone. In this way, target material(s) may be differentiated within a class of materials by a subset of spectral features. As an illustrative example, the characteristic spectrum 310 includes spectral features 320 produced by both saturated hydrocarbon bonds and unsaturated bonds. The features attributable to unsaturated bonds, such as the C≡C stretch or the H—C≡C bend differentiate the characteristic spectrum 310 from that of a fully unsaturated chemical, such as n-hexane ($C_6H_{12}$). In this way, spectral features 320 can be used to distinguish two very similar materials.

The emission spectrum 330, by contrast, shows characteristic emission profiles 340 of a selection of light sources, as a function of intensity plotted against wavelength. Each light source, which may be an LED, a diode laser, or some other narrow-band or monochromatic light source that emits in a wavelength suitable for vibrational spectroscopy, is characterized by a peak wavelength 350 where the emission profile is centered or at its highest. The emission profiles 340 are also characterized by a distribution 355, that can be described by a width parameter such as the full width at the half maximum (FWHM) intensity. The distribution of each emission profile 340 is important, as described in more detail in reference to FIG. 4A, below, in the context of generating the optimized configuration, at least because multiple spectral features 320 may fall within the emission profile 340 of a single light source. Where the light source is not intended for composition analysis, such that an intensity calibrated source is not being generated, the emission profiles 340 may be normalized to the maximum peak intensity 360 of the subset of light sources, relative to a minimum emission intensity 365 of the subset of light sources. In this way, the projection function, described in reference to FIG. 4A, below, will treat each emission profile 340 as a continuous function of wavelength between a minimum intensity of 0 and a maximum intensity of 1, with non-dimensional units of intensity. As illustrated, each emission spectrum 330 for each individual solution may be identified by metadata, such as a label or ID to permit tracking and outputting the individual solution to a searchable database for use in chemical recycling.

Figure 4A:
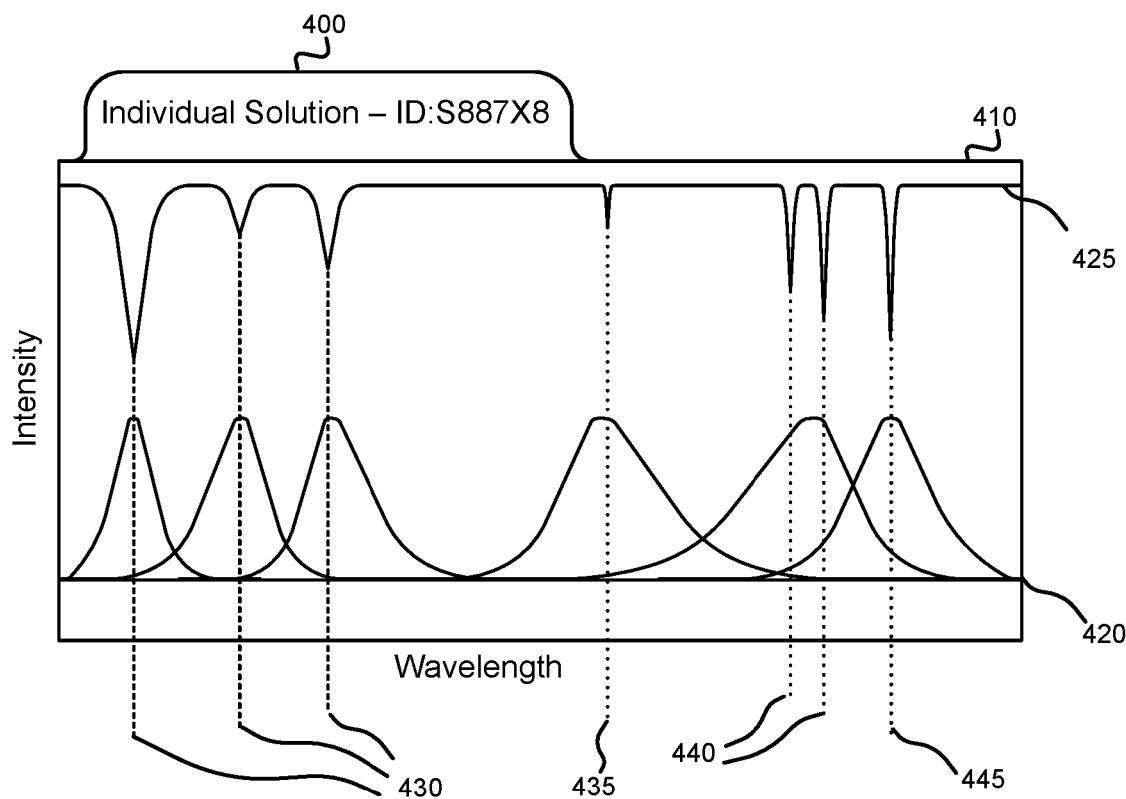
FIGS. 4A and 4B illustrate a projection of a characteristic spectrum onto an emission spectrum for an individual solution and an example workflow for evaluating the individual solution, according to various embodiments.
Figure 4B:
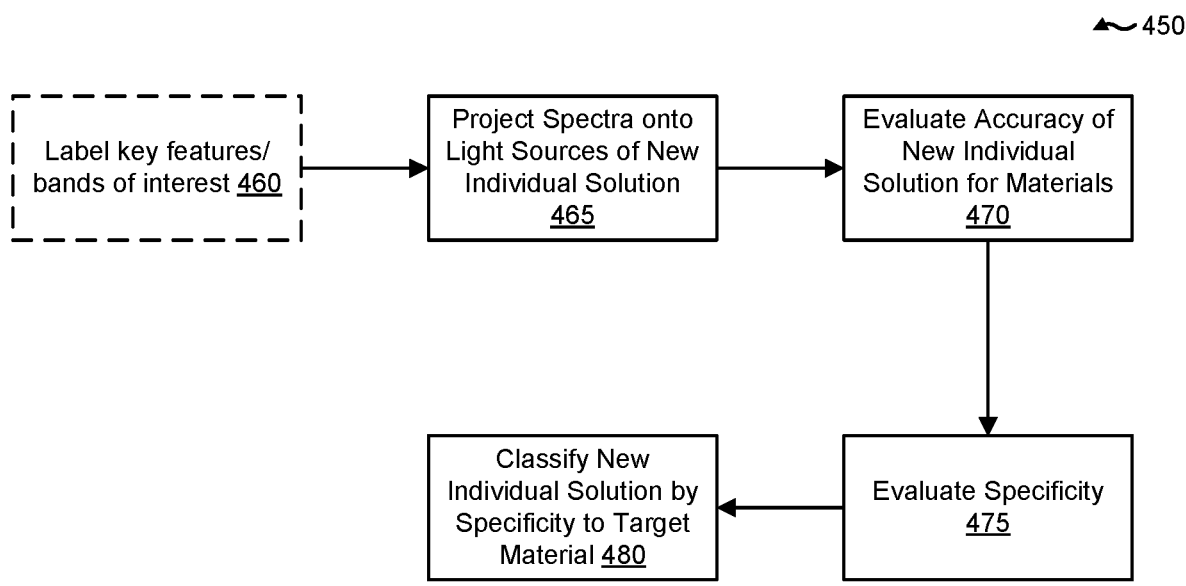

FIGS. 4A-B illustrates a projection 410 of a characteristic spectrum onto an emission spectrum for an individual solution 400 and an example workflow 450 for evaluating the individual solution, according to various embodiments. As part of the processes of the GA, as described in more detail in reference to FIGS. 1-2, the GA evaluates individual solutions using a fitness function. The fitness function may include an approach to estimating the accuracy and specificity of the individual solution 400 to identify, differentiate, or otherwise characterize the target material(s). The fitness function may include procedural approaches for evaluating the individual solution 400, object model based approaches with parameters that may be tuned or adapted to fit a target material, or the GA may include a machine learning model as part of the evaluation, where the model may include a classifier trained to estimate the specificity of individual solution 400 and output a scalar value for use in retention comparison. The individual solution 400, as illustrated in FIG. 4A, may describe a number of light sources, each having a characteristic emission spectrum, such that the individual solution 400 can be described by a combined emission spectrum 420 in the wavelength range over which the target material absorbs radiation used in vibrational spectroscopy, as described by a characteristic absorbance spectrum 425 of the individual solution 400.

An example technique for evaluating the accuracy of the individual solution 400 is by projecting at least a subset of the spectral features included in the characteristic absorbance spectrum 425 onto the emission spectrum 420 of the individual solution 400. The projection 410 refers to an operation where features of the characteristic absorbance spectrum 425, such as peak position or peak width, are projected (denoted by dashed lines) onto the emission spectrum 420 of the individual solution 400, from which the accuracy of the individual solution 400 is evaluated. Evaluating based on the projection 410 can include, but is not limited to, (i) ascertaining an aggregate error in peak position between the emission spectrum 420 and the characteristic absorbance spectrum 425, (ii) ascertaining a degree of coverage, such that bands of interest in the characteristic absorbance spectrum 425 are sufficiently covered by emission from the individual solution 400, or (iii) other techniques that permit the GA to evaluate a scalar value function describing the specificity of the individual solution 400 for the target material represented by the characteristic absorbance spectrum 425.

The emission spectrum 420 includes light sources that address spectral features of the characteristic absorbance spectrum 425 in multiple ways. Depending on the shape of the emission pattern of a light source and the density of features in the characteristic absorbance spectrum 425, light sources may address a single feature or multiple features. The projection 410 also includes light sources where multiple light sources address a single feature. For example, some features 430 are individually addressed by separate light sources, while other features 440 are addressed in common by a single light source. Where the characteristic absorbance spectrum 425 includes a feature 435 that is relatively isolated from other features, but is identified as being within a band of interest, an individual solution light source is addressed to that feature. In some cases, physical phenomena, design constraints, light source availability, or other factors, influence the emission characteristics of light sources, such that a feature 445 or a group of features is addressed by multiple light sources that combine in the emission spectrum 420. Addressing multiple features with a single light source permits a greater number of features or even other bands of interest to be addressed by the individual solution 400, without neglecting any features identified in the characteristic absorbance spectrum, at the potential cost of being unable to distinguish those features that project onto a shared light source. Where the features 440 are produced by the same chemical structure, such as different motions of the same covalent bond, differentiating the features 440 may provide relatively little specificity to the individual solution overall.

The workflow 450 describes operations included in an example approach to evaluating the specificity of the individual solution 400, including the projection 410 of the characteristic absorbance spectrum 425 of the target material onto the emission spectrum 420 of the individual solution 400. The workflow 450 may optionally include labelling key features or bands of interest in the characteristic absorbance spectrum 425 at operation 460. As described in more detail in reference to FIG. 1, the bands of interest identify features of the characteristic absorbance spectrum 425 that differentiate the target material from other materials in the same material class, from other material classes, identify the target material as a contaminant, or disqualify the material from chemical recycling. As an example, a band of interest may include a feature of the characteristic absorbance spectrum 425 that results from crosslinking of a polymeric material. Chemical recycling of a highly cross-linked polymer may include additional processing steps, such as de-polymerization or decomposition, and, as such, identifying spectral features indicative of cross-linking will permit appropriate sorting of waste materials to avoid sending cross-linked polymer materials to processes for which they are not suited.

At operation 465, the characteristic absorbance spectrum 425 is projected onto the emission spectrum 420 of the individual solution 400. The projection 410, illustrated in FIG. 4A, permits a quantitative assessment of the extent to which the emission spectrum 420 addresses the features of the characteristic absorbance spectrum 425. Since some features 430-435 are addressed by a single light source, while other features 440-445 share a light source or are addressed by multiple sources, the accuracy of the individual solution 400 is evaluated holistically at operation 470. The projection may include, but is not limited to, (i) finding a difference spectrum that represents the extent of the features that are not addressed by the emission spectrum 420 or (ii) determining an error value describing the accuracy of the individual solution 400 to address the target material or a class of materials including the target material. For example, if the target material is a member of a base polymer class, the accuracy of individual solution 400 will correspond to whether it addresses the spectral features attributable to atoms present in the polymer class, such as the polymer backbone, but not necessarily those of substituted side chains.

Evaluation of the specificity, at operation 475, describes repeating the accuracy evaluation for grouped spectra of different materials, to elucidate whether the individual solution can be used to separate, identify, or differentiate the target material. For example, if the target material is differentiable by the inclusion of aromaticity in a material class where aromaticity is relatively infrequently observed, the individual solution 400 will be more specific if the emission spectrum 420 includes a light source addressed at features attributable to aromatic bonds. As an illustrative example, such an approach could permit the differentiation of polystyrene from polyethylene waste in a chemical recycling process. Evaluating the specificity, therefore, includes evaluation of the accuracy of the individual solution 400 and estimating a figure of merit by which the individual solution may be classified against its parent individual solutions of the preceding generation. The figure of merit may be a minimum intergroup spacing determined by clustering accuracy values for the individual solution 400, but may also be estimated by other approaches that describe the ability of the individual solution 400 to differentiate the target material. In this way, classifying the individual solution 400 at operation 480 permits the GA implementing the workflow 450 to populate a generation of individual solutions and develop an optimum individual solution for implementation in a chemical recycling process.

FIG. 5 illustrates an example flow describing a method 500 for generating a light source array for identifying a target material, according to various embodiments. As described in reference to FIGS. 1-4, one or more operations making up the method 500 may be executed by a computer system in communication with additional systems including, but not limited to, characterization systems, network infrastructure, databases, and user interface devices. In some embodiments, the method 500 includes operation 505, where the computer system obtains a light source dataset and a spectroscopic dataset. As described in more detail in reference to FIG. 1, obtaining the light source dataset includes accessing, receiving, or otherwise being provided with data for a number of light sources that are available for incorporation into a compound light source or a light source array. The light source dataset may include data describing the individual solution light sources, such as the emission characteristics, power parameters, device size, or logistical availability, all or any of which may be included in determining constraints on generation of individual solution candidate solutions.

The method 500 includes operation 510, where the computer system initializes a genetic algorithm (GA). The GA, as described in more detail in reference to FIGS. 1-2, includes an initialization cycle including populating an initial generation with multiple individual solutions. The individual solutions may be generated by random or pseudo-random combination of light sources, such that the initial generation includes a diverse population, as diversity in the initial population reduces the potential for convergence to a local maximum in the fitness landscape. The light sources in the dataset may be identified by an integer value, such that a chromosome encoding of the individual solutions is represented by a vector encoding a combination of light sources, such as an integer value vector of fixed length where each entry in the vector represents a light source. Initializing the new generation also includes evaluating the individual solutions for specificity to the target material. The specificity evaluation forms the basis for retention of parents, children, in the populating of successive generations.

The method 500 includes operation 515, where the computer system selects a first individual solution and a second individual solution. The selection of the first and second individual solution is made on a random basis. These two individual solutions, also referred to Once selected, the method 500 proceeds to operation 520, where the computer system generates a new individual solution from the first and second individual solutions. Generating the new individual solution, also referred to as the child, includes a crossover operation and may include a mutation operation. Crossover describes any of a number of possible approaches to combining the chromosome encodings of the parent individual solutions to compose the chromosome encoding of the child. For example, the crossover approach may be a single-point crossover where a region of the chromosome encodings of each parent are exchanged. Other approaches, as described in more detail in reference to FIG. 1, may include ordered crossover or multi-point crossover, such that the child represents a different individual solution than the parents. Crossover is subject to constraints, for example, eliminating duplicate light sources or limiting overlap of light source emission patterns.

Alternatively, the child may be generated by cloning one of the parents, rather than crossing the chromosome encodings of two parents. Cloning provides advantages in some cases, where a parent is to be retained across generations, for example, through a list of elite individual solutions. In addition, mutation may be applied to further diversify the child and introduce randomness that reduces the chances of converging to a local optimum rather than the global optimum.

The method 500 includes operation 525, where the computer system evaluates the new individual solution using the spectroscopic dataset. The evaluation of the new individual solution provides the specificity value, which is a scalar value facilitating comparison between the new individual solution and the parent individual solutions. As described in more detail in reference to FIGS. 4A-4B, evaluating the new individual solution using the spectroscopic dataset includes projecting the absorbance spectrum of the target material onto the emission spectrum of the new individual solution and estimating an error value for the projection. By repeating the projection for multiple absorbance spectra onto the emission spectrum of the new individual solution, error value data is clustered into groups that may be labelled by metadata associated with the absorbance spectra. Intergroup distance, an example of a measure of specificity, is measured between the groups and the minimum distance is used as a scalar value by which the new individual solution, the child, is compared to the parents. In this case, the same grouped absorbance spectra may be used in both operation 510 and operation 525, such that the specificity value is directly comparable.

The method 500 includes operation 530, where the computer system adds the new individual solution to a new generation of solutions. Comparison of the specificity of the new individual solution to the target material(s) to that of the parents facilitates the convergence of the GA to the global optimum solution. For the following generation, the new individual solution is retained when the specificity evaluated in operation 525 exceeds that of the parents evaluated in operation 510. The retention of highly specific children shifts the new generation toward an optimum in the fitness landscape. In cases where the child is less specific than one or both parents, the child is discarded and the GA repeats the operations of generating and evaluating a new individual solution.

The method 500 includes operation 535, where the computer system populates the new generation of solutions. Repeating the operations 515-530 permits the GA to populate a new generation, referred to as a new population of solutions. The new generation also includes a number of elite individual solutions that are characterized by high specificity, and that may be replaced by more highly specific children. The retention of elite individual solutions promotes the convergence of the GA in fewer generations, at least in part because elite parents are more likely to produce elite children, and retention criteria involve replacing parents with children. To facilitate retention of elite individual solutions, the GA tracks the specificity of each individual solution and maintains a list of individual solutions with the highest specificity for the target material(s). For example, the GA may retain one fourth or more of each generation with elite individual solutions from the previous generation.

The method 500 includes operation 540, where the computer system iterates the genetic algorithm. As described in more detail in reference to FIGS. 1-2, the GA iterates the population of additional generations until a maximum number of iterations is reached or the specificity of the individual solutions converges to a global optimum of the fitness landscape. Convergence may be estimated by a marginal change in an aggregate specificity of the generation approaching a maximum. For example, the specificity of the generation may asymptotically approach an optimum. That being said, as the specificity of the individual solutions improves with each subsequent generation, the number of repeated processes of operation 535 increases, as the likelihood that a child will outperform its parents becomes less likely. For at least this reason, the number of iterations at 540 may be limited based on other factors, such as specificity exceeding a threshold value or a pre-defined number of cycles.

The method 500 includes operation 545, where the computer system identifies one or more implementation individual solutions. In the final generation, which satisfies the termination criteria of the GA, one or more individual solutions are selected for implementation as a light source array. Multiple individual solutions may be selected, for example, where the specificity is equivalent, or where the individual solutions incorporate different light sources. Identifying multiple implementation individual solutions, therefore, improves the robustness of the GA approach by anticipating and potentially overcoming logistical factors, such as unavailability of constituent light sources.

The method 500 includes operation 550, where the computer system outputs the one or more implementation individual solutions. As part of outputting the implementation individual solution(s), the computer system may generate light source configuration instructions, for example, to reconfigure an adaptive light source array including multiple addressable light sources. Alternatively, the computer system may generate a light source configuration for a rapid prototyping process or an assembly system to fabricate or build a light source according to the chromosome encoding of the implementation individual solution(s). In this way, the light source may include multiple light sources, such as LEDs so that the target material(s) may be differentiated by vibrational spectroscopy, without relying on broad-spectrum interferometric techniques.

III. SYSTEM ENVIRONMENT

Figure 6:
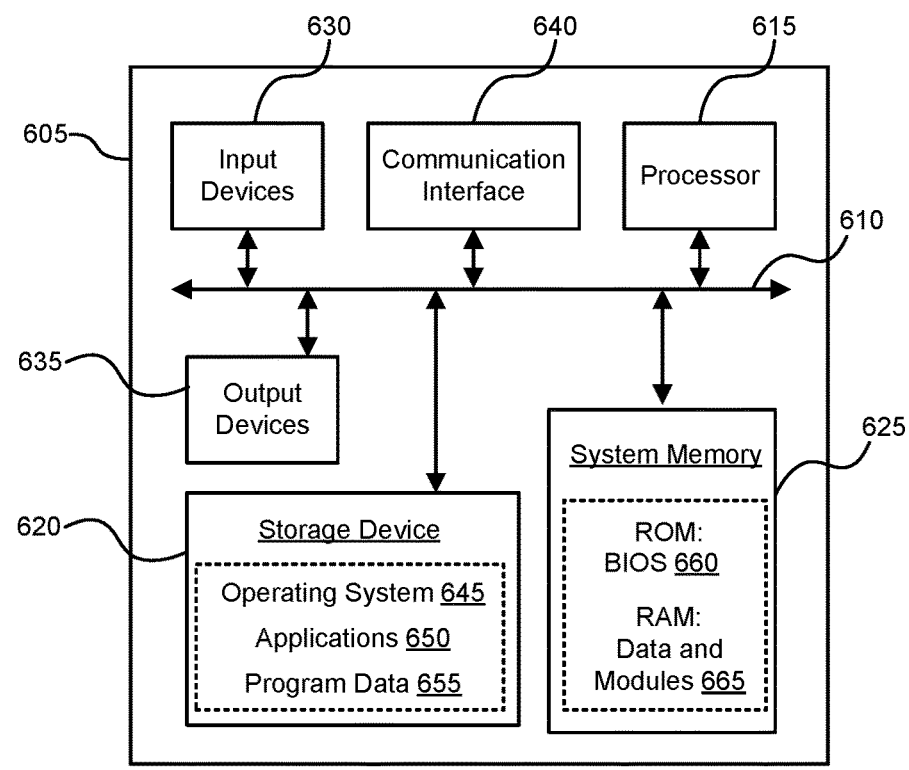
FIG. 6 is an illustrative architecture of a computing system implemented as some embodiments of the present disclosure.

FIG. 6 is an illustrative architecture of a computing system 600 implemented as some embodiments of the present disclosure. The computing system 600 is only one example of a suitable computing system and is not intended to suggest any limitation as to the scope of use or functionality of the present disclosure. Also, computing system 600 should not be interpreted as having any dependency or requirement relating to any one or combination of components illustrated in computing system 600.

As shown in FIG. 6, computing system 600 includes a computing device 605. The computing device 605 can be resident on a network infrastructure such as within a cloud environment, or may be a separate independent computing device (e.g., a computing device of a service provider). The computing device 605 may include a bus 610, processor 615, a storage device 620, a system memory (hardware device) 625, one or more input devices 630, one or more output devices 635, and a communication interface 640.

The bus 610 permits communication among the components of computing device 605. For example, bus 610 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 605.

The processor 615 may be one or more processors, microprocessors, or specialized dedicated processors that include processing circuitry operative to interpret and execute computer readable program instructions, such as program instructions for controlling the operation and performance of one or more of the various other components of computing device 605 for implementing the functionality, steps, and/or performance of the present disclosure. In certain embodiments, processor 615 interprets and executes the processes, steps, functions, and/or operations of the present disclosure, which may be operatively implemented by the computer readable program instructions. For example, processor 615 can retrieve, e.g., import and/or otherwise obtain or access absorbance spectra and light source data, encode the absorbance spectra and light source data, implement GA operations as described, and generate an optimized light source configuration to differentiate a target material from other materials for sorting processes as part of chemical recycling. In embodiments, the information obtained or generated by the processor 615, e.g., chromosome encodings for individual solutions describing light sources, can be stored in the storage device 620.

The storage device 620 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 605 in accordance with the different aspects of the present disclosure. In embodiments, storage device 620 may store operating system 645, application programs 650, and program data 655 in accordance with aspects of the present disclosure.

The system memory 625 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 660 (BIOS) including the basic routines that help to transfer information between the various other components of computing device 605, such as during start-up, may be stored in the ROM. Additionally, data and/or program modules 665, such as at least a portion of operating system 645, program modules, application programs 650, and/or program data 655, that are accessible to and/or presently being operated on by processor 615, may be contained in the RAM. In embodiments, the program modules 665 and/or application programs 650 can comprise, for example, a processing tool to identify and annotate spectrum and light source data, a metadata tool to append data structures with metadata, and genetic algorithm tools to generate optimized light source configurations, which provides the instructions for execution of processor 615.

The one or more input devices 630 may include one or more mechanisms that permit an operator to input information to computing device 605, including, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 635 may include one or more mechanisms that output information to an operator, such as, but not limited to, audio speakers, headphones, audio line-outs, visual displays, antennas, infrared ports, tactile feedback, printers, or combinations thereof.

The communication interface 640 may include any transceiver-like mechanism (e.g., a network interface, a network adapter, a modem, or combinations thereof) that enables computing device 605 to communicate with remote devices or systems, such as a mobile device or other computing devices such as, for example, a server in a networked environment, e.g., cloud environment. For example, computing device 605 may be connected to remote devices or systems via one or more local area networks (LAN) and/or one or more wide area networks (WAN) using communication interface 640.

As discussed herein, computing system 600 may be configured to implement a genetic algorithm to generate an optimized light source configuration to specifically differentiate a target material from other non-target materials. In particular, computing device 605 may perform tasks (e.g., process, steps, methods and/or functionality) in response to processor 615 executing program instructions contained in non-transitory machine readable storage medium, such as system memory 625. The program instructions may be read into system memory 625 from another computer readable medium (e.g., non-transitory machine readable storage medium), such as data storage device 620, or from another device via the communication interface 640 or server within or outside of a cloud environment. In embodiments, an operator may interact with computing device 605 via the one or more input devices 630 and/or the one or more output devices 635 to facilitate performance of the tasks and/or realize the end results of such tasks in accordance with aspects of the present disclosure. In additional or alternative embodiments, hardwired circuitry may be used in place of or in combination with the program instructions to implement the tasks, e.g., steps, methods and/or functionality, consistent with the different aspects of the present disclosure. Thus, the steps, methods and/or functionality disclosed herein can be implemented in any combination of hardware circuitry and software.

IV. ADDITIONAL CONSIDERATIONS

In the preceding description, various embodiments have been described. For purposes of explanation, specific configurations and details have been set forth in order to provide a thorough understanding of the embodiments. However, it will also be apparent to one skilled in the art that the embodiments may be practiced without the specific details. Furthermore, well-known features may have been omitted or simplified in order not to obscure the embodiment being described. While example embodiments described herein center on polymeric materials, these are meant as non-limiting, illustrative embodiments. Embodiments of the present disclosure are not limited to such materials, but rather are intended to address material processing operations for which a wide array of materials serve as potential feedstocks for a material recycling and/or up-cycling process. Such materials may include, but are not limited to, metals, bio-polymers such as ligno-cellulosic materials, visco-elastic materials, minerals such as rare earth containing materials, as well as complex composite materials or devices.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes and workflows disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the description to provide a thorough understanding of the embodiments. However, it will be understood that the embodiments may be practiced without these specific details. For example, specific computational models, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method for selecting a spectroscopic sensor light source configuration, the method comprising:
   obtaining, by a computer system, a light source dataset describing a plurality of light sources and a spectroscopic dataset describing a plurality of materials;
   initializing, by the computer system, a genetic algorithm with an initial generation of solutions, an individual solution of the initial generation of solutions comprising a subset of light sources of the plurality of light sources;
   selecting, by the computer system using the genetic algorithm, a first individual solution and a second individual solution from the initial generation of solutions, the first and second individual solutions respectively described by a first chromosome encoding and a second chromosome encoding;
   generating, by the computer system using the genetic algorithm, a new individual solution from the first and second individual solutions by combining the first chromosome encoding and the second chromosome encoding;
   evaluating, by the computer system using the genetic algorithm, a specificity of the new individual solution to a target material of the plurality of materials;
   in accordance with the specificity of the new individual solution to the target material surpassing a specificity of the first individual solution to the target material or a specificity of the second individual solution to the target material: adding, by the computer system using the genetic algorithm, the new individual solution to a new generation of solutions;
   populating, by the computer system using the genetic algorithm, the new generation of solutions with a plurality of new individual solutions;
   generating, by the computer system using the genetic algorithm, one or more subsequent generations of solutions by iterating the genetic algorithm;
   selecting, by the computer system using the genetic algorithm, one or more implementation individual solutions from a final generation of the one or more subsequent generations by identifying the one or more implementation individual solutions exhibiting a threshold specificity to the target material; and
   outputting, by the computer system, the one or more implementation individual solutions, wherein an implementation individual solution of the one or more implementation individual solutions comprises a spectroscopic sensor light source configuration.

2. The method of claim 1, wherein evaluating the new individual solution comprises:
   inputting the new individual solution into a classifier model implemented in an artificial neural network;
   inputting the spectroscopic dataset into the classifier model, the spectroscopic dataset comprising a plurality of spectra from a plurality of material classifications; and
   evaluating, for the new individual solution using the classifier model, a lowest intergroup distance between a first material classification comprising the target material and a second material classification excluding the target material,
   wherein the lowest intergroup distance describes the specificity of the new individual solution to the target material relative to one or more other materials.

3. The method of claim 2, wherein evaluating the specificity of the new individual solution to the target material comprises:
   generating a plurality of projections by projecting the plurality of spectra onto the subset of light sources making up the new individual solution;
   generating a plurality of accuracy values using the plurality of projections;
   mapping the plurality of accuracy values onto a feature space;
   identifying one or more clusters of accuracy values in the feature space; and
   evaluating a plurality of intergroup distances between the one or more clusters of accuracy values.

4. The method of claim 3, wherein the spectroscopic dataset comprises a plurality of FTIR absorbance spectra for the plurality of materials categorized into the plurality of material classifications.

5. The method of claim 1, wherein the subset of light sources comprises ten light sources, respectively described by a central wavelength and a wavelength range.

6. The method of claim 1, wherein evaluating, by the computer system, the first and second individual solutions is based in part on an output of a fitness function, the fitness function indicative of the specificity of the first and second individual solutions to the target material.

7. The method of claim 1, wherein generating the new individual solution comprises deduplicating the subset of light sources by removing duplicate light sources contributed to the new individual solution from both the first individual solution and the second individual solution.

8. The method of claim 1, further comprising:
   retaining an individual solution across the one or more subsequent generations when a specificity of the individual solution to the target material exceeds a threshold.

9. The method of claim 1, wherein the target material comprises a type-standard of a class of materials, a specific material within the class of materials, an additive, a contaminant, a constituent material, or a composite material.

10. The method of claim 1, wherein outputting the one or more implementation individual solutions comprises:
    providing an implementation individual solution of the one or more implementation individual solutions to an assembly system configured to build a spectroscopic sensor light source from a spectroscopic sensor light source configuration; and building, according to the implementation individual solution of the one or more implementation individual solutions, the spectroscopic sensor light source.

11. The method of claim 1, wherein outputting the one or more implementation individual solutions comprises:
configuring a spectroscopic sensor light source of a material screening system according to an implementation individual solution of the one or more implementation individual solutions;
screening a waste material stream, using the spectroscopic sensor light source, for the target material; and
selecting the target material from the waste material stream.

12. The method of claim 1, wherein the spectroscopic dataset comprises a plurality of FTIR absorbance spectra for the plurality of materials categorized into a plurality of material classifications.

13. The method of claim 12, wherein the target material is polyethylene terephthalate, cross-linked polyethylene, or low density polyethylene.

14. The method of claim 13, wherein the plurality of materials comprises polyvinyl chloride, polystyrene, or poly-lactic acid polymers.

15. A method for configuring a spectroscopic sensor light source cascade, the method comprising:
obtaining, by a computer system, a light source dataset describing a plurality of light sources and a spectroscopic dataset describing a plurality of materials;
identifying a primary target material and a secondary target material of the plurality of materials;
generating, by the computer system using a first genetic algorithm, a primary implementation individual solution exhibiting a threshold specificity to the primary target material, wherein generating the primary implementation individual solution comprises:
    selecting a first individual solution and a second individual solution from a first initial generation of solutions, the first and second individual solutions respectively described by a first chromosome encoding and a second chromosome encoding,
    generating a first new individual solution from the first and second individual solutions by combining the first chromosome encoding and the second chromosome encoding,
    adding the first new individual solution to a first new generation of solutions,
    populating the first new generation of solutions with a plurality of first new individual solutions,
    generating one or more subsequent first generations of solutions by iterating the first genetic algorithm, and
    selecting the primary implementation individual solution from a first final generation of the one or more subsequent first generations by identifying the primary implementation individual solution exhibiting a first threshold specificity to the primary target material; and
generating, by the computer system using a second genetic algorithm, a secondary implementation individual solution exhibiting a threshold specificity to the secondary target material, wherein generating the secondary implementation individual solution comprises:
    selecting a third individual solution and a fourth individual solution from a second initial generation of solutions, the third and fourth individual solutions respectively described by a third chromosome encoding and a fourth chromosome encoding,
    generating a second new individual solution from the third and fourth individual solutions by combining the third chromosome encoding and the fourth chromosome encoding,
    adding the second new individual solution to a second new generation of solutions,
    populating the second new generation of solutions with a plurality of second new individual solutions,
    generating one or more subsequent second generations of solutions by iterating the second genetic algorithm, and
    selecting the secondary implementation individual solution from a second final generation of the one or more subsequent second generations by identifying the secondary implementation individual solution exhibiting a second threshold specificity to the secondary target material; and
outputting, by the computer system, the primary implementation individual solution and the secondary implementation individual solution, wherein:
    the primary target material comprises a first material class and the secondary target material comprises a first member of the first material class;
    the primary implementation individual solution is generated to differentiate the first material class from a second material class; and
    the secondary implementation individual solution is generated to differentiate the first member of the first material class from a second member of the first material class.

16. The method of claim 15, wherein generating the primary implementation individual solution further comprises:
identifying one or more bands of interest from the spectroscopic dataset associated with the primary target material;
initializing, by the computer system, the first genetic algorithm with the first initial generation of solutions, the first individual solution of the first initial generation of solutions comprising a subset of light sources of the plurality of light sources; and
evaluating, by the computer system using the first genetic algorithm, a specificity of the first new individual solution to the primary target material based in part on the one or more bands of interest,
wherein adding the first new individual solution to the first new generation of solutions is in accordance with the specificity of the first new individual solution to the primary target material surpassing a specificity of the first individual solution to the primary target material or a specificity of the second individual solution to the primary target material.

17. The method of claim 16, wherein evaluating the specificity of the first new individual solution to the primary target material comprises:
generating a plurality of projections by projecting a plurality of spectra of the spectroscopic dataset onto a subset of light sources of the plurality of light sources making up the first new individual solution;
generating a plurality of accuracy values using the plurality of projections;
mapping the plurality of accuracy values onto a feature space;
identifying one or more clusters of accuracy values in the feature space;
evaluating a plurality of intergroup distances between the one or more clusters of accuracy values; and evaluating a lowest intergroup distance from the plurality of intergroup distances,
wherein the lowest intergroup distance describes the specificity of the first new individual solution to the primary target material relative to one or more other materials.

18. The method of claim 15, wherein the spectroscopic dataset comprises a plurality of FTIR absorbance spectra for the plurality of materials categorized into a plurality of material classifications.

19. The method of claim 15, wherein the second genetic algorithm is the first genetic algorithm.

20. A non-transitory computer readable storage medium storing instructions that, when executed by one or more processors of a computer system, cause the one or more processors to:
obtain, by a computer system, a light source dataset describing a plurality of light sources and a spectroscopic dataset describing a plurality of materials;
initialize, by the computer system, a genetic algorithm with an initial generation of solutions, an individual solution of the initial generation of solutions comprising a subset of light sources of the plurality of light sources;
select, by the computer system using the genetic algorithm, a first individual solution and a second individual solution from the initial generation of solutions, the first and second individual solutions respectively described by a first chromosome encoding and a second chromosome encoding;
generate, by the computer system using the genetic algorithm, a new individual solution from the first and second individual solutions by combining the first chromosome encoding and the second chromosome encoding;
evaluate, by the computer system using the genetic algorithm, a specificity of the new individual solution to a target material of the plurality of materials;
in accordance with the specificity of the new individual solution to the target material surpassing a specificity of the first individual solution to the target material or a specificity of the second individual solution to the target material: add, by the computer system using the genetic algorithm, the new individual solution to a new generation of solutions;
populate, by the computer system using the genetic algorithm, the new generation of solutions with a plurality of new individual solutions;
generate, by the computer system using the genetic algorithm, one or more subsequent generations of solutions by iterating the genetic algorithm;
select, by the computer system using the genetic algorithm, one or more implementation individual solutions from a final generation of the one or more subsequent generations by identifying the one or more implementation individual solutions exhibiting a threshold specificity to the target material; and
output, by the computer system, the one or more implementation individual solutions, wherein an implementation individual solution of the one or more implementation individual solutions comprises a spectroscopic sensor light source configuration.

21. The computer readable storage medium of claim 20, wherein the target material is a primary target material, the genetic algorithm is a first genetic algorithm, the one or more implementation individual solutions comprise a primary implementation individual solution, and wherein the instructions, when executed by the one or more processors, further cause the one or more processors to:
generate, by the computer system using a second genetic algorithm, a secondary implementation individual solution exhibiting a threshold specificity to a secondary target material; and
outputting, by the computer system, the secondary implementation individual solution, wherein:
the primary target material comprises a first material class and the secondary target material comprises a first member of the first material class;
the primary implementation individual solution is generated to differentiate the first material class from a second material class; and
the secondary implementation individual solution is generated to differentiate the first member of the first material class from a second member of the first material class.

22. The computer readable storage medium of claim 20, wherein evaluating the specificity of the new individual solution to the target material comprises:
generating a plurality of projections by projecting a plurality of spectra of the spectroscopic dataset onto a subset of light sources of the plurality of light sources making up the new individual solution;
generating a plurality of accuracy values using the plurality of projections;
mapping the plurality of accuracy values onto a feature space;
identifying one or more clusters of accuracy values in the feature space;
evaluating a plurality of intergroup distances between the one or more clusters of accuracy values; and
evaluating a lowest intergroup distance from the plurality of intergroup distances,
wherein the lowest intergroup distance describes the specificity of the new individual solution to the target material relative to one or more other materials.

23. The computer readable storage medium of claim 22, wherein the subset of light sources comprises ten light sources, respectively described by a central wavelength and a wavelength range.

24. The computer readable storage medium of claim 22, wherein the spectroscopic dataset comprises a plurality of FTIR absorbance spectra for the plurality of materials categorized into a plurality of material classifications.

* * * * *